Figure 1A:
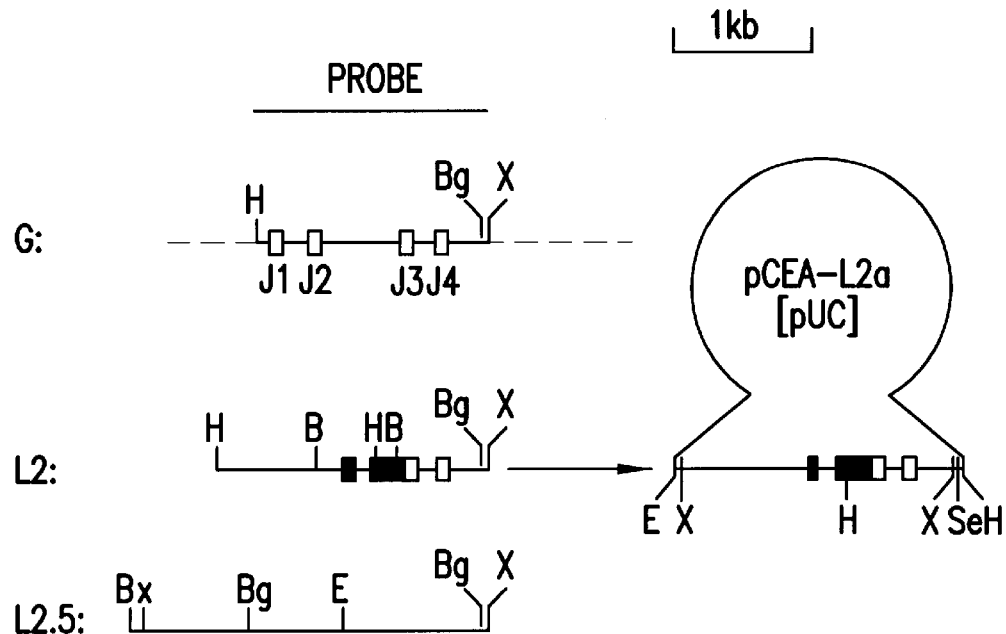

United States Patent [19]
Hardman et al.

[11] Patent Number: 6,020,153
[45] Date of Patent: Feb. 1, 2000

[54] CHIMERIC ANTIBODIES

[75] Inventors: Norman Hardman; Laura Lee Gill, both of Riehen, Switzerland; Ronald F. J. de Winter, Milton Ernest, United Kingdom; Kathrin Wagner, Basel; Christoph Heusser, Bottmingen, both of Switzerland

[73] Assignee: Ciba-Geigy Corporation, Tarrytown, N.Y.

[21] Appl. No.: 08/307,087

[22] Filed: Sep. 16, 1994

Related U.S. Application Data

[63] Continuation of application No. 07/947,897, Sep. 18, 1992, abandoned, which is a continuation of application No. 07/287,178, Dec. 21, 1988, abandoned.

[30] Foreign Application Priority Data

Jan. 5, 1988 [GB] United Kingdom .................... 8800077
Aug. 24, 1988 [GB] United Kingdom .................... 8820099

[51] Int. Cl.$^7$ .............................. C12N 15/00; C12N 5/00; C12P 21/06; C07H 21/04; C12D 21/08
[52] U.S. Cl. .................. 435/69.1; 435/172.3; 435/240.2; 536/23.1; 536/23.53; 530/387.7
[58] Field of Search ................................ 435/172.3, 69.1; 536/23.53; 530/387.7

[56] References Cited

U.S. PATENT DOCUMENTS

| | | | |
|---|---|---|---|
| 4,816,397 | 3/1989 | Boss et al. | 435/68 |
| 4,816,567 | 3/1989 | Cabilly et al. | 530/307 |
| 4,978,745 | 12/1990 | Shoemaker et al. | 530/387 |
| 5,047,507 | 9/1991 | Buchegger et al. | 530/387 |
| 5,225,539 | 7/1993 | Winter et al. | 530/387.3 |

FOREIGN PATENT DOCUMENTS

| | | |
|---|---|---|
| 0 098 162 | 11/1984 | European Pat. Off. |
| 0 125 023 | 11/1984 | European Pat. Off. |
| 0 171 496 | 2/1986 | European Pat. Off. |
| 0 173 494 | 3/1986 | European Pat. Off. |
| 0 216 846 | 4/1987 | European Pat. Off. |
| 0 256 654 | 2/1988 | European Pat. Off. |
| 0 332 424 | 9/1989 | European Pat. Off. |
| WO 86/01533 | 3/1986 | WIPO . |
| WO 87/02671 | 5/1987 | WIPO . |
| WO 89/00999 | 2/1989 | WIPO . |
| WO/8900999 | 2/1989 | WIPO . |

OTHER PUBLICATIONS

Hardman et al Int. J. Cancer 44:424, 1989.
Ex parte Andersen 212 USPQ 100, 1981.
G. L. Boulianne et al., Nature, vol. 312, 643 (1984).
M.S. Neuberger et al., Nature, vol. 314, 268 (1985).
B. G. Sahagan et al., J. vol. 137, 1066 (1986).
L. K. Sun et al., Proc. Natl. Acad. Sci., vol. 84, 214 (1987).
A. Y. Liu et al., Proc. Natl, Acad Sci., vol. 84, 3439 (1987).
C. B. Beidler et al., J. Immunol., vol. 141, 4053 (1988).
Wagner et al., The Journal of Immunology, 130(5): 2308–2315 (1983).
Wagner et al., The Journal of Immunology, 130(5):2302–2307 (1983).
Copy of International Search Report, Oct. 31, 1988.
Beidler et al., "Cloning and High Level Expression of a Chimeric Antibody with Specificity for Human Carcinoembryonic Antigen", The Journal of Immunology, 141(11): 4053–4060 (1988).
Boulianne et al., "Production of functional chimaeric mouse/human antibody", Nature, 312: 643–646 (1984).
Buchegger et al., "Radioimmunotherapy of Human Colon Carcinoma by $^{131}$I–Labelled Monoclonal Anti–cea Antibodies in a Nude Mouse Model", Int. J. Cancer, 41: 127–134 (1988).
Cabilly et al., "Generation of antibody activity from immunoglobulin polypeptide chains produced in *Escherichia coli*," Proc. Natl. Acad. Sci. USA, 81: 3273–3277 (1984).
Hardman et al., "Generation of a Recombinant Mouse–Human Chimaeric Monoclonal Antibody Directed Against Human Carcinoembryonic Antigen", Int. J. Cancer, 44: 424–433 (1989).
Liu et al., "Chimeric mouse–human IgG1 antibody that can mediate lysis of cancer cells", Proc. Natl. Acad. Sci. USA, 84: 3439–3443 (1987).
Neuberger et al., "A hapten–specific chimaeric IgE antibody with human physiological effector function", Nature, 314: 268–270 (1985).
Sahagan et al., "A Genetically Engineered Murine/Human Chimeric Antibody Retains Specificity for Human Tumor–Associated Antigen," The Journal of Immunology, 137(3): 1066–1074 (1986).
Sun et al., "Chimeric antibody with human constant regions and mouse variable regions directed against carcinoma–associated antigen 17–1A," Proc. Natl. Acad. Sci. USA, 84: 214–218 (1987).
Wagener et al., "Monoclonal Antibodies for Carcinoembryonic Antigen and Related Antigens as a Model System: Determination of Affinities and Specificities of Monoclonal Antibodies by Using Biotin–Labeled Antibodies and Avidin as Precipitating Agent in a Solution Phase Immunoassay", The Journal of Immunology, 130(5): 2302–2307 (1983).
Wagener et al., "Monoclonal Antibodies for Carcinoembryonic Antigen and Related Antigens as a Model System: A Systematic Approach for the Determination of Epitope Specificities of Monoclonal Antibodies", The Journal of Immunology, 130(5): 2308–2315 (1983).

*Primary Examiner*—Suzanne E. Ziska
*Attorney, Agent, or Firm*—Henry P. Nowak; James Scott Elmer; Shawn P. Foley

[57] ABSTRACT

The invention relates to murine/human chimeric monoclonal antibodies with high specificity to and affinity for human carcinoembryonic antigen (CEA), derivatives thereof, processes for the preparation of these antibodies and their derivatives, DNAs coding for heavy and light chains of these antibodies, processes for the preparation of said DNAs, mammalian cell lines that produce and secrete the antibodies and processes for the preparation of said cell lines. The chimeric antibodies and their derivatives are used for clinical purposes in vitro and in vivo, especially for the diagnosis of cancer, for localization and in vivo imaging of tumors, for therapy, e.g. site-directed delivery of cytotoxins, and similar purposes. The invention also concerns test kits and pharmaceutical compositions containing said chimeric monoclonal antibodies and/or derivatives thereof.

25 Claims, 7 Drawing Sheets

CHIMERIC ANTIBODIES

This application is a continuation, of application Ser. No. 07/947,897, filed Sep. 18, 1992 now abandoned which is a continuation of Ser. No. 07/287,178, filed Dec. 21, 1988 now abandoned.

FIELD OF THE INVENTION

This invention relates to mouse/human chimeric monoclonal antibodies with high specificity to and affinity for human carcinoembryonic antigen (CEA), derivatives thereof, processes for the preparation of these antibodies and their derivatives, DNAs coding for heavy and light chains of these antibodies, processes for the preparation of said DNAs, mammalian cell lines that produce and secrete the antibodies, processes for the preparation of said cell lines, the use of the chimeric monoclonal antibodies and their derivatives for the diagnosis and therapy of cancer, test kits containing the chimeric monoclonal antibodies, and pharmaceutical preparations containing said antibodies.

BACKGROUND OF THE INVENTION

Immunoglobulins (antibodies) play an important role in the immune system of mammals. They are produced by plasma cells and consist of two identical light (L) polypeptide chains and two identical heavy (H) polypeptide chains joined by disulfide bridges, or polymers of this basic four chain unit. The light chains are of type $\kappa$ or $\lambda$, the heavy chains of type $\mu$, $\delta$, $\gamma$, $\alpha$ or $\epsilon$. Each chain consists of a variable (V) region and a constant (C) region. The V-regions, which show considerable sequence differences in antibodies with different specificity, comprise highly variable parts, so-called hypervariable or complementarity determining regions (CDRs), flanked by relatively conserved parts, so-called framework regions (FRs).

Antibodies are bifunctional molecules. On the one hand, the N-terminal variable segments of the H- and L-chain polypeptides associate in a highly specific and individual manner, generating a three-dimensional structure with a unique affinity for particular chemical motifs (epitopes) on the surface of an antigen, i.e. a molecule which is recognized as foreign by the organism and induces an immune response. Such epitopes can be small-molecular-weight molecules (haptens) or parts of macromolecular chemical structures such as proteins, carbohydrates and glycoproteins, e.g. cell-surface antigens.

The unique antigen-combining characteristics of the immunoglobulin (Ig) molecule results from genetic recombination of H- and L-chain germline genes early in B-cell differentiation, for example during embryogenesis: one of several hundred V-segments is joined to one of a small number of joining segments (J-segments) and, in the case of the H-chain locus, additional diversity segments (D-segments), forming a totally unique contiguous V-(D)-J rearranged gene segment coding for an Ig molecule with specific antigen-combining characteristics. In addition to antibody diversity caused by simple gene recombination, the precise junction at which V and J segment genes combine may vary slightly. As the joining reaction can occur between different base pairs and additional nucleotides can be added during the recombination process, several different amino acids, not coded in the germline, can be inserted at the site of each potential V-J or D-J combination. Furthermore, somatic mutation of single bases also contributes to Ig diversity.

The other key structural feature of Ig molecules is their ability to activate diverse biological pathways in the immune system. These so-called effector functions (complement binding, stimulation of phagocytosis, triggering of granule release by mast cells) reside primarily in the carboxy-terminal constant region segments of the H-chain polypeptides, giving rise to different Ig classes (IgA, IgE, IgG, etc.) which define the role of the antibody in a particular immune response.

The development of hybridoma technology has made it possible to generate continuous cell lines, mostly murine hybridomas, producing monoclonal antibodies of desired specificity which can be used to identify, isolate and characterize biologically important molecules. However, a major limitation in the use of murine-derived monoclonal antibodies as in vivo diagnostic and therapeutic agents is their immunogenicity as foreign proteins, their rather long persistence in the circulation, and the formation of damaging immune complexes. On the other hand, the treatment with human monoclonal antibodies is limited also since human hybridoma cell lines are rarely available, usually unstable and do not produce monoclonal antibodies of appropriate specificity in sufficient quantities and at reasonable costs.

A promising alternative is the modification of immunoglobulin genes by using recombinant DNA technology. One approach to decrease immunogenicity and to avoid undesired immune response, for example, is the production of chimeric antibodies with the advantages and the selectivity of murine monoclonals, yet the species specific properties of human antibodies.

The overall strategies applicable for the assembly of chimeric genes and the production of chimeric antibodies involve standard procedures of recombinant DNA technology (identification and isolation of Ig genes, insertion of the cloned genes into vectors, transfection into immortalized cell lines, expression of chimeric proteins). Depending on the source of the genes to be combined and on the nature of the genes coding for the antigen-specific variable region, however, particular problems arise so that new and inventive steps are required to develop workable solutions.

Several research groups have attempted to engineer chimeric antibodies. Their research objectives differ in the conceptual approach, however, and the research results vary considerably with regard to the nature and characteristics of the recombinant molecules.

Chimeric antibodies of several immunoglobulin classes have been produced.

Neuberger et al. (Nature 314, 268, 1985) describe a chimeric IgE$\lambda$1 antibody whose heavy chain is composed of a human e constant region fused to a mouse variable region specific for the hapten 4-hydroxy-3-nitrophenacetyl (NP). The strategy used in the production of the chimeric antibody is to construct a chimeric gene coding for the heavy chain and to introduce this chimeric DNA segment into the J558L mouse cell line in which the expressed chimeric heavy chain is assembled with the endogenous mouse light chain to produce complete IgE molecules.

Boulianne et al. (Nature 312, 643, 1984) succeeded in linking the variable regions of the heavy and light chains from an anti-TNP mouse myeloma to human $\mu$ and $\kappa$ genes, respectively. The chimeric genes were transfected into myeloma cells. The secreted IgM, however, was not as effective as the original mouse IgM and showed different binding qualities.

The generation of chimeric immunoglobulin G by joining human $\gamma$ constant genes to murine variable genes has been described by various authors.

Patent application WO 87/02671 describes a chimeric antibody which binds to viral antigens, especially hepatitis B surface antigen, created from a human γ1 region and a variable region from mouse myeloma CRL 8017. The authors also constructed a mouse/human chimeric antibody on the basis of the mouse monoclonal antibody (MAb) L6, as did Liu et al. (Proc. Natl. Acad. Sci. 84, 3439, 1987). MAb L6 [IgG2a(κ)] binds to a carbohydrate antigen found on the surface of cells derived from a variety of human carcinomas. The authors give exact data for the human colon carcinoma cell line C-3347. The γ2a and κ constant regions of MAb L6 were substituted by human γ1 and κ constant regions by recombining cDNA modules encoding variable or constant region domains.

Another chimeric monoclonal antibody directed to the surface antigens of human carcinomas was constructed by Sahagan et al. (J. Immunol. 137, 1066, 1986) who fused variable region exons from the IgG1 antibody of the murine hybridoma cell line B6.2 to human γ1/κ genes. Binding characteristics for the chimeric Ig were determined with A549.E1 human lung carcinoma cells.

Sun et al. (Proc. Natl. Acad. Sci. 84, 214, 1987) combined DNA fragments coding for the H-chain/L-chain variable regions of anti-colorectal carcinoma (ACRC) antibody, produced by mouse hybridoma 1083-17-A, with human γ3/Cκ regions.

The chimeric MAbs which are subject of the present invention are directed against carcinoembryonic antigen (CEA). CEA is a complex immunoreactive glycoprotein with a molecular weight of 180,000 found in adenocarcinomas of endodermally derived digestive system epithelia and foetal colon. The role of CEA immunoassays for diagnosis and serially monitoring cancer patients for recurrent disease or response to therapy has been widely evaluated and documented. One of the major drawbacks of the use of anti-CEA antibodies for the above purposes has been the cross-reactivity of these reagents with some apparently normal adult tissues.

Previous studies have shown that most conventional hyperimmune antisera raised against CEA using different immunogens cross-react with many different types of carcinomas as well as CEA-related antigens, e.g. non-specific cross-reacting antigen NCA, tumor-extracted CEA-related antigen TEX, various normal faecal antigens (NFA1, NFA2), biliary glycoprotein-I and others, found in normal colonic mucosa, spleen, liver, lung, sweatglands, polymorphonuclear leukocytes and monocytes of apparently normal individuals (for an overview, cf. Herberman & McIntire, "Immunodiagnosis of Cancer", Vol. 9, part 1, N.Y., 1979). This means that the antisera recognize epitopes specific for CEA alone as well as epitopes present on both CEA and CEA-related antigens; it further suggests closely related genes between CEA and CEA-related antigens as well as precursor-product relationships between some of them.

It is suggested that polyclonal antibodies (rabbit, sheep) recognize 10–15 antigenic sites in CEA (Sundblad et al., Protides Biol. Fluids 24, 435, 1976). The epitopes are predominantly located on the peptide moieties of CEA and appear to be strongly conformation dependent. Using monoclonal antibodies, at least 5 different epitopes were detected in CEA (Hedin et al., Mol. Immunol. 23, 1053, 1986).

Anti-CEA monoclonal antibodies have already been employed for the production of chimeric antibodies. In patent application EP 0 125 023, an Igγ1 antibody originating from hybridoma cell line CEA.66-E3 is used. The chimeric antibody is not characterized with regard to epitope specificity or cross-reactivity nor are binding or inhibition data included. The inventors describe the use of *E. coli* for the cloning of DNA fragments and the expression of the chimeric genes. It is well established, however, that prokaryotic cells do not provide the necessary steps for biosynthesis of functional tetrameric antibodies, such as correct nascent polypeptide chain folding, glycosylation and assembly. The inventors of EP 0 125 023 describe (Proc. Natl. Acad. Sci. 81, 3273, 1984) that no detectable antibody activity is found in *E. coli* coproducing IgG H- and L-chains for the original mouse antibody when prepared following the guidance of the patent specification. The specification lists a number of possible host cells, also including mammalian cells, but these suggestions are not substantiated by the examples. The conceptual approach to the production of chimeric antibodies in the above cited patent application therefore lacks the basis for the expression of the recombinant gene constructs and thus, the secretion of active monoclonal antibodies.

OBJECT OF THE INVENTION

The object of the invention is the construction of novel chimeric monoclonal antibodies (MAbs) which possess murine variable and human constant region determinants, bind specifically to human carcinoembryonic antigen, are produced at a high level in immortalized mammalian cell lines, can be used for diagnostic and therapeutic purposes.

In view of the complex antigenic structure of the CEA molecule, the desired chimeric anti-CEA MAbs must have the following characteristics:

high affinity for CEA, high percentage of binding to CEA-carrying carcinoma cells, both in vitro and in vivo, low percentage or absence of binding to normal tissues and cells.

DESCRIPTION OF THE INVENTION

The invention concerns chimeric monoclonal antibodies consisting of variable regions of mouse origin and human constant regions, which recognize human carcinoembryonic antigen (CEA), and derivatives thereof.

The invention relates especially to chimeric monoclonal antibodies and derivatives thereof which recognize epitopes of CEA not present on non-specific cross-reacting antigen NCA, such as $NCA_{56}$ and $NCA_{95}$ (Buchegger et al., Int. J. Cancer 33, 643, 1984), on biliary glycoprotein, or on granulocytes.

Preferred are chimeric monoclonal antibodies and derivatives thereof with an affinity of at least $2.1 \times 10^{10}$ liters/mol for human CEA.

For the production of a chimeric monoclonal antibody, a chimeric light chain and a chimeric heavy chain, each comprising a variable and a constant region, are constructed separately and are therefore distinguished in this description with special emphasis on the variable region of each chimeric construct.

The preferred chimeric monoclonal antibody of the invention and its derivatives are characterized in that they comprise light chain variable regions of the formula

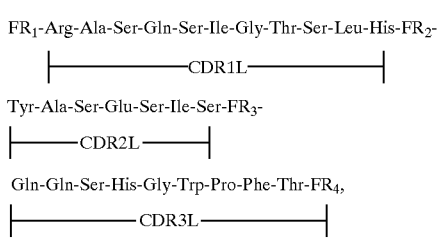

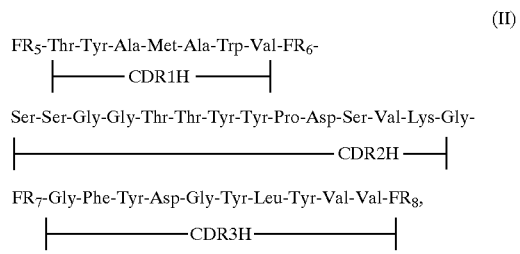

wherein $FR_1$ is a polypeptide residue comprising 23–28 naturally occurring amino acids, $FR_2$ is a polypeptide residue comprising 14–16 naturally occurring amino acids, $FR_3$ is a polypeptide residue comprising 30–34 naturally occurring amino acids and $FR_4$ is a polypeptide residue comprising 9–11 naturally occurring amino acids, and wherein the amino acid Cys may be in the oxidized state forming S-S-bridges. Especially preferred are a chimeric monoclonal antibody and derivatives thereof comprising light chain variable regions of formula I, wherein the polypeptide residues of the framework regions $FR_1$, $FR_2$, $FR_3$ and $FR_4$ are those preferably occurring in mammalian, especially murine, antibodies.

Most preferred are a chimeric monoclonal antibody and derivatives thereof according to the invention comprising light chain variable regions of formula I, wherein $FR_1$ is a polypeptide residue of the formula A-Gly-Asp-Ile-Leu-Leu-Thr-Gln-Ser-Pro-Ala-Ile- (IA)

Leu-Ser-Val-Ser-Pro-Gly-Glu-Arg-Val-Thr-Phe-
Ser-Cys, wherein A is hydrogen, acyl, or the residue Ala-Ser-Arg, Ser-Arg or Arg, particularly hydrogen,
$FR_2$ is the polypeptide residue Trp-Tyr-Gln-Gln-Arg-Thr-Asn-Gly-Ser-Pro-Arg- (IB)

Leu-Leu-Met-Lys, $FR_3$ is the polypeptide residue

Gly-Ile-Pro-Ser-Arg-Phe-Ser-Gly-Ser-Gly- (IC)

Ser-Gly-Thr-Asp-Phe-Thr-Leu-Thr-Ile-Asn-

Ser-Val-Glu-Ser-Glu-Asp-Ile-Ala-Asp-Tyr-

Tyr-Cys, and $FR_4$ is the polypeptide residue

Phe-Gly-Ser-Gly-Gly-Thr-Lys-Leu-Glu-Ile-Lys, (ID)

and wherein the amino acid Cys may be in the oxidized state forming S-S-bridges.

The invention also relates to a chimeric monoclonal antibody and derivatives thereof comprising light chain variable regions of formula I, wherein $FR_1$, $FR_2$, $FR_3$ and $FR_4$ are polypeptide residues of formula IA, IB, IC and ID, respectively, and wherein one or more, e.g. 1, 2, 3 or 4, single amino acids are replaced by other amino acids outside the regions CDR1L, CDR2L and CDR3L, and wherein the amino acid Cys may be in the oxidized state forming S-S-bridges.

The preferred chimeric monoclonal antibody of the invention and its derivatives are characterized in that they comprise heavy chain variable regions of the formula wherein $FR_5$ is a polypeptide residue comprising 32–36 naturally occurring amino acids, $FR_6$ is a polypeptide residue comprising 14–16 naturally occurring amino acids, $FR_7$ is a polypeptide residue comprising 32–34 naturally occurring amino acids and $FR_8$ is a polypeptide residue comprising 12–14 naturally occurring amino acids, and wherein the amino acid Cys may be in the oxidized state forming S-S-bridges. Especially preferred are a chimeric monoclonal antibody and derivatives thereof comprising heavy chain variable regions of formula II, wherein the polypeptide residues of the framework regions $FR_6$, $FR_7$, $FR_8$ and $FR_9$ are those preferably occurring in mammalian, especially murine, antibodies.

Most preferred are a chimeric monoclonal antibody and derivatives thereof according to the invention comprising heavy chain variable regions of formula II, wherein $FR_5$ is a polypeptide residue of the formula B-Gly-Val-Gln-Cys-Glu-Val-Lys-Leu-Val-Glu- (IIA)

Ser-Gly-Gly-Gly-Leu-Val-Lys-Pro-Gly-Gly-

Ser-Leu-Lys-Leu-Ser-Cys-Ala-Ala-Ser-Gly-

Phe-Thr-Phe-Arg, wherein B is hydrogen or acyl, particularly hydrogen,
$FR_6$ is the polypeptide residue Arg-Gln-Thr-Pro-Glu-Lys-Arg-Leu-Glu-Trp- (IIB)

Val-Thr-Ser-Ile, $FR_7$ is the polypeptide residue

Arg-Phe-Thr-Ile-Ser-Arg-Asp-Asn-Ala-Arg- (IIC)

Asn-Ile-Leu-Tyr-Leu-Gln-Val-Ser-Ser-Leu-

Arg-Ser-Asp-Thr-Ala-Tle-Tyr-Tyr-Cys-Ala-

Arg, and $FR_8$ is the polypeptide residue

Asp-Tyr-Trp-Gly-Gln-GLy-Thr-Ser-Leu-Thr- (IID)

Val-Ser-Ser, and wherein the amino acid Cys may be in the oxidized state forming S-S-bridges.

The invention also relates to a chimeric monoclonal antibody and derivatives thereof comprising heavy chain variable regions of formula II, wherein $FR_5$, $FR_6$, $FR_7$ and $FR_8$ are polypeptide residues of formula IIA, IIB, IIC and IID, respectively, and wherein one or more, e.g. 1, 2, 3 or 4, single amino acids are replaced by other amino acids outside the regions CDR1H, CDR2H and CDR3H, and wherein the amino acid Cys may be in the oxidized state forming S-S-bridges.

Light chain variable regions of formula IA and heavy chain variable regions of formula IIA may comprise and acyl residue, for example formyl or alkanoyl, e.g. palmitoyl, myristoyl or lower alkanoyl, such as acetyl or propionyl.

The class of an Ig molecule is defined by the H- and L-chain constant regions as pointed out above. A chimeric monoclonal anti body of the invention may be of any immunoglobulin class, i.e. IgA, IgD, IgE, IgG or IgM. A preferential chimeric monoclonal antibody according to the invention is an immunoglobulin of class G which comprises light chain human constant regions κ or λ, especially human constant regions κ, and heavy chain human constant regions γ1, γ2, γ3 or γ4, especially human constant regions γ4.

The invention preferentially concerns a chimeric monoclonal antibody and derivatives thereof with light chain variable regions of formula I with the preferred meaning, wherein the amino acid Cys may be in the oxidized state forming S-S-bridges, light chain human constant regions κ, heavy chain variable regions of formula II with the preferred meaning, wherein the amino acid Cys may be in the oxidized state forming S-S-bridges, and heavy chain human constant regions γ4.

Derivatives of chimeric monoclonal antibodies according to the invention are, for example, fragments that retain their specificity for the antigenic determinants of the CEA molecule, such as the univalent fragment Fab and the divalent fragment F(ab')$_2$, conjugates of the chimeric monoclonal antibodies with enzymes, fluorescent markers, metal chelates, cytostatic or cytotoxic substances, avidin, biotin, and the like, and radioactively labelled antibodies.

Enzymes used for antibody conjugates of the invention are, for example horseradish peroxidase, alkaline phosphatase, β-D-galactosidase, glucose oxidase, glucoamylase, carbonic anhydrase, acetylcholinesterase, lysozyme, malate dehydrogenase or glucose-6-phosphate dehydrogenase.

Fluorescent markers conjugated with chimeric antibodies are fluorescein, fluorochrome, rhodamine, and the like.

In such conjugates the antibody is bound to the enzymes or fluorescent markers directly or by the way of a spacer or linker group.

Examples for metal chelators are ethylenediaminetetraacetic acid (EDTA), diethylenetriaminepentaacetic acid (DPTA), 1,4,8,11-tetraazatetradecane, 1,4,8,11-tetraazatetradecane-1,4,8,11-tetraacetic acid, 1-oxa-4,7,12,15-tetraazaheptadecane-4,7,12,15-tetraacetic acid, or the like. Cytostatics, applicable in connection with the chimeric antibodies, are, inter alia, alkylating substances, such as mechlorethamine, triethylenephosphoramide, cyclophosphamide, ifosfamide, chlorambucil, busulfan, melphalan or triaziquone, also nitrosourea compounds, such as carmustine, lomustine, or semustine. Also used are antimetabolites, such as methotrexate, mercaptopurine, cytarabine, fluorouracil, floxuridine, or ftorafur. A further group of cytostatics includes vinblastine and vincristine, as well as certain antibiotics, such as actinomycin-D, daunorubicin (daunomycin), doxorubicin, mithramycin, streptonigrin, mitomycin and bleomycin. Further suitable cytostatics are, inter alia, procarbacine, hydroxyurea, L-asparaginase, dacarbazine, mitotane, estramustine, or podophyllotoxin. Further cytostatic agents are hormones and hormone antagonists, such as corticosteroids, e.g. prednisone, progestins, e.g. hydroxyprogesterone or medroprogesterone, estrogens, e.g. diethylstilbestrol, antiestrogens, e.g. tamoxifen, androgens, e.g. testosterone, and aromatase inhibitors, e.g. aminogluthetimide.

Conjugates of chimeric monoclonal antibodies with cytotoxic substances contain either the intact toxin or the A-chain derived from it. Toxins suitable for antibody-coupling are, among others, several lectins, such as ricin or abrin, or diphtheria toxin A, and the like.

Radioactively labelled chimeric monoclonal antibodies contain e.g. radioactive iodine ($^{123}$I, $^{125}$I, $^{131}$I), yttrium ($^{90}$Y), technetium ($^{99m}$Tc), or the like.

The chimeric monoclonal antibodies and derivatives thereof according to the invention are prepared by processes that are known per se, characterized in that mammalian cells as defined further below producing such chimeric monoclonal antibodies are multiplied according to known methods in vitro or in vivo, and, if desired, the resulting monoclonal antibodies are converted into derivatives thereof.

Multiplication in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growth-sustaining supplements, e.g. feeder cells such as normal mouse peritoneal exudate cells, spleen cells, bone marrow macrophages, or the like.

As the antibody-producing cells carry a selection marker described in detail hereinbelow, the culture media may be supplemented with selective media, for example media containing G-418 or xanthine, hypoxanthine/thymidine and mycophenolic acid, in order to prevent normal cells from overgrowing the producer cells.

In vitro production allows scale-up to give large amounts of the desired antibodies. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges.

The cell culture supernatants are screened for the desired monoclonal antibodies, preferentially with an enzyme immunoassay, e.g. a dot-assay, or a radioimmunoassay.

For isolation of the chimeric monoclonal antibodies, the immunoglobulins in the culture supernatants are first concentrated, e.g. by precipitation with ammonium sulphate, dialysis against hygroscopic material such as PEG, filtration through selective membranes, or the like. If necessary and/or desired, the concentrated antibodies are purified by the customary chromatography methods, for example gel filtration, ion-exchange chromatography, chromatography over DEAE-cellulose or (immuno-)affinity chromatography.

Large quantities of the desired chimeric monoclonal antibodies can also be obtained by multiplying the cells in vivo. For this purpose, cell clones from a histocompatible and/or tolerated Ig-producing cell line are injected into syngeneic mammals to cause growth of antibody-producing tumors. Optionally, the animals are primed with a hydrocarbon, especially mineral oils such as pristane (tetramethyl pentadecane), prior to the injection. After 1–3 weeks, the antibodies are isolated from the body fluids of those mammals. For example, hybridoma cells derived from Balb/c mice that produce the desired chimeric monoclonal antibodies are injected intraperitoneally into Balb/c mice that have optionally been pre-treated with a hydrocarbon such as pristane, and, after 8–10 days, ascitic fluid is taken from these animals. The chimeric monoclonal antibodies are isolated therefrom by conventional methods as given above.

Fragments of chimeric monoclonal antibodies that retain their specificity towards human CEA, for example Fab or F(ab')$_2$ fragments, can be obtained from a chimeric antibody prepared as described above by methods known per se, e.g. by genetic manipulation of the appropriate Ig-coding exons, by digestion with enzymes such as papain or pepsin, and/or cleavage of disulfide bonds by chemical reduction.

Conjugates of monoclonal antibodies of the invention are prepared by methods known in the art, e.g. by reacting a monoclonal antibody prepared as described hereinbefore with the enzyme in the presence of a coupling agent, e.g. glutaraldehyde, periodate, N,N'-o-phenylenedimaleimide, N-(m-maleimidobenzoyloxy)-succinimide, N-(3-[2'-pyridyldithio]-propionoxy)-succinimide, N-ethyl-N'-(3-dimethylaminopropyl)-carbodiimide or the like. Conjugates with avidin are prepared likewise. Conjugates with biotin are prepared e.g. by reacting monoclonal antibodies with an activated ester of biotin such as the biotin N-hydroxysuccinimide ester. Conjugates with fluorescent markers are prepared in the presence of a coupling agent, e.g. those listed above, or by reaction with an isothiocyanate, preferably fluorescein-isothiocyanate. Conjugates of the chimeric antibodies of the invention with cytostatic/cytotoxic substances and metal chelates are prepared in an analogous manner.

Chimeric monoclonal antibodies radioactively labelled with iodine ($^{123}$I, $^{125}$I, $^{131}$I) are obtained from the monoclonal antibodies according to the invention by iodination known per se, for example with radioactive sodium or potassium iodide and a chemical oxidising agent, such as sodium hypochlorite, chloramine T or the like, or an enzymatic oxidising agent, such as lactoperoxidase, glucose oxidase and glucose. Chimeric monoclonal antibodies according to the invention are coupled to yttrium ($^{90}$Y) for example by diethylenetriaminepentaacetic acid (DTPA)-chelation. Technetium-99m labelled chimeric antibodies are prepared by ligand exchange processes, for example by reducing pertechnate (TcO$_4^-$) with stannous ion solution, chelating the reduced technetium onto a Sephadex column and applying the antibodies to this column, or by direct labelling techniques, e.g. by incubating pertechnate, a reducing agent such as SnCl$_2$, a buffer solution such as a sodium-potassium phthalate-solution, and the antibodies.

The invention also concerns recombinant DNAs comprising an insert coding for a light chain murine variable region and/or for a heavy chain murine variable region of chimeric monoclonal antibodies specific for human CEA as described hereinbefore. By definition such DNAs comprise coding single stranded DNAs, double stranded DNAs consisting of said coding DNAs and of complementary DNAs thereto, or these complementary (single stranded) DNAs themselves.

In particular the invention concerns a recombinant DNA comprising an insert coding for a light chain murine variable region specific for human CEA, originating from genomic DNA of the cell line CE 25. The cell line CE 25 was generated by the fusion of B lymphocytes of the spleen of Balb/c mice and cells from the myeloma P3-NS2/1Ag4 and produces a murine anti-CEA antibody with a κ light chain and a γ1 heavy chain.

Preferred is a recombinant DNA comprising an insert coding for the polypeptide of formula I, optionally containing introns, especially an insert coding for the polypeptide of formula I wherein FR$_1$, FR$_2$, FR$_3$ and FR$_4$ are polypeptide residues of formula IA, IB, IC and ID, respectively, optionally containing introns.

An example of such a preferred recombinant DNA is a recombinant DNA comprising an insert of the formula

```
                                                                                          (III)
        TCTAGACTGCTGTGGTCTTTTAAGTAGCATGAAAAACATCTCGCTAAAGAAGGAATTAGTT
    1   ---------+---------+---------+---------+---------+---------+   60

TGAACATGCTAGAAATACATCTGTGATACTCTCATCACTCTTGTTGGAAAGATATGCAAG
   61   ---------+---------+---------+---------+---------+---------+   120

AAGCACTATTTGGCTATTATTTGGAAAGTGCTATAATGTATTTTGATATCTCAACCTCTG
  121   ---------+---------+---------+---------+---------+---------+   180

AAATTCTTCTGTATGTTGGCAGATTGTAAACCTTTACAAGGCTTTCATTCTCTTCTCTGG
  181   ---------+---------+---------+---------+---------+---------+   240

AGAAAAATGTCTTTGTAGGCAATCCAGAATTTCTTATTTCTTGCTAATGAAATCTCCTCA
  241   ---------+---------+---------+---------+---------+---------+   200

GTGTGATATCACTTTAGTTTCATGTGTTGTTATGCTTCATGTAATGTTAAGAAAGTTAAA
  301   ---------+---------+---------+---------+---------+---------+   360

GATGCTCCAATCCATATTGTAAGAAACATTCCAAGCCATGGAATAAGGCATGGATTTGAG
  361   ---------+---------+---------+---------+---------+---------+   420

ATGCTCTTTATTTCAAACTACTGAATATATCTTAGAGATTTCTTTAGACTGTGTTAAATA
  421   ---------+---------+---------+---------+---------+---------+   480

TGTAACCATTTAAGTAGGAGTCAAGTCTCCTTTAAATCTCAACAGCTCTTCAGGTAACCA
  481   ---------+---------+---------+---------+---------+---------+   540

ACAAAAGGATAAATATTCTAATAAGTCACTAGGAGCATGCTCTTCTGACCAGGTCTTTCT
  541   ---------+---------+---------+---------+---------+---------+   600

TATAAGCAACATGAAGACAGTATGATTTGCATAAGTTTTTCTTTCTTCTAATGTCCCTGC
  601   ---------+---------+---------+---------+---------+---------+   660

CTCTTAGAGTATTATAAGAAGATCTTTCTAGGGATGTGTCATGGTCCACACAAAAATAGG
  661   ---------+---------+---------+---------+---------+---------+   720

M   V   S   T   P   Q   F   L   V   F   L   L   F   W   I   P
                       MetValSerThrProGlnPheLeuValPheLeuLeuPheTrpIlePro
        GAAAGTGTGAAGATGGTATCCACACCTCAGTTCCTTGTATTTTTGCTTTTCTGGATTCCA
  721   ---------+---------+---------+---------+---------+---------+   780
```

-continued

```
      GGTAATGACTGTTTGGGTGTGGCAAAAAAGTGGAGATGTTATTTAAATACAAAATTTTCT
 781  ---------+---------+---------+---------+---------+---------+   740

TGCTTTATTTGGAAGCCAATGTCACATGGGAATTGACTTTCAGTTTAAAGAAATTGATAC
 841  ---------+---------+---------+---------+---------+---------+   900

AATAAAAGTCATTTATTTTTCTAAGTTGTTTAGAAGTGACTTTCATATTCAGTGTTATGA
 901  ---------+---------+---------+---------+---------+---------+   960

A   S   R   G   D   I   L   L   T   Q   S
                                       AlaSerArgGlyAspIleLeuLeuThrGlnSer
      TCGACTAATGTATCTTCCATTTTTCCAGCCTCCAGAGGTGACATCTTGCTGACTCAGTCT
 961  ---------+---------+---------+---------+---------+---------+  1020

P   A   I   L   S   V   S   P   G   E   R   V   T   F   S   C   R   A   S   Q
      ProAlaIleLeuSerValSerProGlyGluArgValThrPheSerCysArgAlaSerGln
      CCAGCCATCCTGTCTGTGAGTCCAGGAGAAAGAGTCACTTTCTCCTGCAGGGCCAGTCAG
1021  ---------+---------+---------+---------+---------+---------+  1080

S   I   G   T   S   L   H   W   Y   Q   Q   R   T   N   G   S   P   R   L   L
      SerIleGlyThrSerLeuHisTrpTyrGlnGlnArgThrAsnGlySerProArgLeuLeu
      AGCATTGGCACAAGCTTACACTGGTATCAGCAAAGAACAAATGGTTCTCCAAGGCTTCTC
1081  ---------+---------+---------+---------+---------+---------+  1140

M   K   Y   A   S   E   S   I   S   G   I   P   S   R   F   S   G   S   G   S
      MetLysTyrAlaSerGluSerIleSerGlyIleProSerArgPheSerGlySerGlySer
      ATGAAGTATGCTTCTGAGTCTATCTCTGGGATCCCTTCCAGGTTTAGTGGCAGTGGATCA
1141  ---------+---------+---------+---------+---------+---------+  1200

G   T   D   F   T   L   T   I   N   S   V   E   S   E   D   I   A   D   Y   Y
      GlyThrAspPheThrLeuThrIleAsnSerValGluSerGluAspIleAlaAspTyrTyr
      GGGACAGATTTTACTCTTACCATCAATAGTGTGGAGTCTGAAGATATTGCAGATTATTAC
1201  ---------+---------+---------+---------+---------+---------+  1260

C   Q   Q   S   H   G   W   P   F   T   F   G   S   G   T   K   L   E   I   K
      CysGlnGlnSerHisGlyTrpProPheThrPheGlySerGlyThrLysLeuGluIleLys
      TGTCAACAAAGTCATGGCTGGCCATTCACGTTCGGCTCGGGGACAAAGTTGGAAATAAAA
1261  ---------+---------+---------+---------+---------+---------+  1320

CGTAAGTGGACTTTTGTTCATTTACTTGTGACGTTTTGGTTCTGTTTGGGTAGCTTGTGT
1321  ---------+---------+---------+---------+---------+---------+  1380

GAATTTGTGATATTT
1201  ---------+-----  1395.
```

A recombinant DNA comprising an insert of formula III wherein one or more, e.g. up to 10, single nucleotides are replaced by other nucleotides outside the nucleotide sequences of formula III from position 1069-1102, 1147-1167 and 1263-1291, respectively, is also preferential.

In particular, the invention also concerns a recombinant DNA comprising an insert coding for a heavy chain murine variable region specific for human CEA, originating from genomic DNA of the cell line CE 25.

Preferred is a recombinant DNA comprising an insert coding for the polypeptide of formula II, optionally containing introns, especially an insert coding for the polypeptide of formula II wherein $FR_5$, $FR_6$, $FR_7$ and $FR_8$ are polypeptide residues of formula IIA, IIB, IIC and IID, respectively, optionally containing introns.

An example of such a preferred recombinant DNA is a recombinant DNA comprising an insert of the formula

```
                                                                                                 (IV)
      AAGCTTGTTCTGTTCACATGCAAGGAGGGAAACTAAACTGAGTATGGTGAATCCCTAACC
   1  ---------+---------+---------+---------+---------+---------+   60

AAAGGGAAAAAATGAAACTACAATATGTTTCAAATGCTGTAACTGAAATCTGGTTTTTTG
  61  ---------+---------+---------+---------+---------+---------+   120

ATGCCTTATATCTGGTATCATCAGTGACTTCAGATTTAGTCCAACCCCAGAGCATGGTAT
 121  ---------+---------+---------+---------+---------+---------+   180

AGCAGGAAGACATGCAAATAAGTCTTCTCTCTGCCCATGAAAACACCTCGGCCCTGACCC
 181  ---------+---------+---------+---------+---------+---------+   240

TGCAGCTCTGACAGAGGAGGCCAGTCCATGGATTTGAGTTCCTCACATTCAGTGATGAGC
 241  ---------+---------+---------+---------+---------+---------+   300

M   N   F   G   F   S   L   I   F   L   V   L   V
                                        MetAsnPheGlyPheSerLeuIlePheLeuValLeuVal
      ACTGAACACAGACACCTCACCATGAACTTCGGGTTCAGCTTGATTTTCCTTGTCCTTGTT
 301  ---------+---------+---------+---------+---------+---------+   360
```

-continued

```
      L   K   G
      LeuLysGly
      TTAAAAGGTAATTTATTGAGAAGAGATGACATCTATTTTACGCACATGAGACAGAAAAAA
  361 ---------+---------+---------+---------+---------+---------+  420

V   Q
                                                              ValGl
      TGTGGTTTGTTTTGTTAGTGACAGTTTTCCAACCAGTTATTCTCTGTTTGTAGGTGTCCA
  421 ---------+---------+---------+---------+---------+---------+  480

C   E   V   K   L   V   E   S   G   G   G   L   V   K   P   G   G   S   L   K
      nCysGluValLysLeuValGluSerGlyGlyGlyLeuValLysProGlyGlySerLeuLy
      GTGTGAAGTGAAGCTGGTGGAGTCTGGGGGAGGCTTAGTGAAGCCTGGAGGGTCCCTGAA
  481 ---------+---------+---------+---------+---------+---------+  540

L   S   C   A   A   S   G   F   T   F   R   T   Y   A   M   A   W   V   R   Q
      sLeuSerCysAlaAlaSerGlyPheThrPheArgThrTyrAlaMetAlaTrpValArgGl
      ACTCTCCTGTGCAGCCTCTGGGTTCACTTTCAGGACCTATGCCATGGCTTGGGTTCGCCA
  541 ---------+---------+---------+---------+---------+---------+  600

T   P   E   K   R   L   E   W   V   T   S   I   S   S   G   G   T   T   Y   Y
      nThrProGluLysArgLeuGluTrpValThrSerIleSerSerGlyGlyThrThrTyrTy
      GACTCCAGAGAAGAGGCTGGAGTGGGTCACATCCATTAGTAGTGGTGGTACCACCTACTA
  601 ---------+---------+---------+---------+---------+---------+  660

P   D   S   V   K   G   R   F   T   I   S   R   D   N   A   R   N   I   L   Y
      nProAspSerValLysGlyArgPheThrIleSerArgAspAsnAlaArgAsnIleLeuTy
      TCCAGACAGTGTGAAGGGCCGATTCACCATCTCCAGAGATAATGCCAGGAACATCCTGTA
  661 ---------+---------+---------+---------+---------+---------+  720

L   Q   V   S   S   L   R   S   E   D   T   A   I   Y   Y   C   A   R   G   F
      rLeuGlnValSerSerLeuArgSerGluAspThrAlaIleTyrTyrCysAlaArgGlyPh
      CCTGCAAGTGAGCAGTCTGAGGTCTGAGGACACGGCCATTTATTACTGTGCAAGAGGTTT
  721 ---------+---------+---------+---------+---------+---------+  780

Y   D   G   Y   L   Y   V   V   D   Y   W   G   Q   G   T   S   L   T   V   S
      eTyrAspGlyTyrLeuTyrValValAspTyrTrpGlyGlnGlyThrSerLeuThrValSe
      CTATGATGGTTACCTCTATGTTGTGGACTACTGGGGTCAAGGAACCTCACTCACCGTCTC
  781 ---------+---------+---------+---------+---------+---------+  840

S
      rSer
      CTCAGGTAAGAATGGCC
  841 ---------+------- 857.
```

A recombinant DNA comprising an insert of formula IV wherein one or more, e.g. up to 10, single nucleotides are replaced by other nucleotides outside the nucleotide sequences of formula IV from position 575-595, 629-680 and 776-805, respectively, is also preferential.

For the assembly of complete tetrameric immunoglobulin molecules and the expression of active antibodies, the recombinant DNA inserts coding for light and heavy chain variable regions are fused with the corresponding DNAs coding for light and heavy chain constant regions, then incorporated into hybrid vectors and transferred into appropriate host cells with the help of these hybrid vectors.

The invention therefore also concerns recombinant DNAs comprising an insert coding for a light chain murine variable region specific for human CEA fused to a human constant region κ or λ. Preferred is a recombinant DNA coding for a preferred murine variable region as described hereinbefore fused to a human constant region κ.

Likewise the invention concerns recombinant DNAs comprising an insert coding for a heavy chain murine variable region specific for human CEA fused to a human constant region γ, for example γ1, γ2, γ3 or γ4. Preferred is a recombinant DNA coding for a preferred murine variable region as described hereinbefore fused to a human constant region γ4.

Furthermore the invention concerns a recombinant DNA which is a hybrid vector comprising an insert coding for a chimeric murine/human light chain as described hereinbefore and/or an insert coding for a chimeric murine/human heavy chain as described hereinbefore, a complete replicon and one or more dominant marker sequences, operationally linked to expression control sequences.

The markers allow for selection of host cells which contain the vector. Selection markers include genes which confer resistance to heavy metals, e.g. copper, antibiotics, e.g. G-418 (geneticin, a neomycin-derivative) or hygromycin, or genes which complement a genetic lesion of the host cell such as the absence of thymidine kinase, hypoxanthine phosphoryl transferase, dihydrofolate reductase or the like. In addition, hybrid vectors optionally contain signal sequences, one or more restriction sites available for the insertion of a structural gene, enhancers and/or expression control sequences. A wide variety of transcriptional and translational regulatory sequences may be employed, depending on the nature of the host. Preferred vectors are suitable for mammalian hosts and are based on viral replication systems, such as simian virus 40 (SV40), Rous sarcoma virus (RSV), adenovirus 2, bovine papilloma virus (BPV), papovavirus BK mutant (BKV), or mouse and human cytomegalovirus (CMV). Alternatively, the vectors may contain promoters from mammalian expression products, such as actin, collagen, myosin etc., or the native promoter and control sequences which are normally associated with the immunoglobulin gene sequences. Enhancers are transcription-stimulating DNA sequences of viral origin, e.g. derived from simian virus such as SV40, polyoma virus, bovine papilloma virus or Moloney sarcoma virus, or of genomic, especially murine origin (mouse Ig enhancer). An origin of replication is provided either by construction of the vector to include an exogeneous origin, such as derived from SV40 or another viral source, or by the host cell chromosomal replication mechanism. Examples of preferred vectors are those derived from pSV-vectors in which the selectable marker is placed under the control of the SV40 early promoter, in particular pSV2gpt carrying the xanthine-guanine phosphoribosyl transferase gene, and pSV2neo, carrying the phosphotransferase gene.

The chimeric gene constructs for the light chain and for the heavy chain are sequentially or simultaneously transferred into the host cells with the help of two vectors. Alternatively, both heavy and light chains are cloned into the same hybrid vector and incorporated in a one step-procedure as a single construct into the host cells.

The recombinant DNAs coding for the desired chimeric monoclonal antibodies can be prepared, for example, by culturing a transformed host.

In particular, such DNAs can be prepared by
a) isolating murine DNAs from a suitable hybridoma cell line, selecting the desired DNAs coding for the variable regions of monoclonal antibodies directed against human CEA using DNA probes,
b) isolating human DNAs from a genomic library, selecting the desired DNAs coding for the constant regions of monoclonal antibodies using DNA probes,
c) constructing chimeric mouse/human genes by incorporating the DNA of step a) and b) into appropriate hybrid vectors,
d) transferring the obtained hybrid vectors into a recipient host, and
e) selecting and culturing the transformed host.

The DNA according to step a) of the process described above can be obtained by isolation of genomic DNA or by preparation of cDNA from isolated mRNA. As genomic DNA constructs facilitate gene expression, the preparation and use of genomic DNA is to be preferred. Genomic DNA from hybridoma cells is isolated by methods known in the art which include steps for disruption of the cells, e.g. by lysis in presence of detergents like Triton, extracting the DNA, e.g. by treatment with phenol and $CHCl_3$/isoamyl alcohol, and DNA-precipitation. The DNA is fragmented, conveniently by one or more restriction endonucleases, e.g. XbaI, BglII, EcoRI, HindIII, BamHI, the resulting fragments are replicated on a suitable carrier, e.g. nitrocellulose membranes, and screened with a DNA probe as described in more detail hereinbelow for the presence of the DNA sequences coding for the polypeptide sequence of interest, in particular for the presence of the rearranged H- and L-chain Ig gene loci. By this procedure DNA fragments are found that contain inserts with heavy chain V, D and J regions and light chain V and J regions, respectively, together with a leader sequence and introns, if any.

Genomic human DNA according to step b) of the process described above is isolated from suitable human tissue, preferably from human placenta or human foetal liver cells, according to methods known in the art. A genomic DNA library is constructed therefrom by limited digestion with suitable restriction endonucleases, e.g. HaeIII and AluI, and incorporation into λ Charon phage, e.g. λ Charon 4a, following established procedures. The genomic DNA library is replicated, e.g. on nitrocellulose membranes, and screened with a DNA probe as described below for the DNA sequences of interest.

The DNA probe for the mouse variable regions or the human constant regions may be a synthetic DNA, a cDNA derived from mRNA coding for the desired immunoglobulin or a genomic DNA or DNA fragment of known nucleotide sequence. Preferably a genomic DNA or DNA fragment probe is used. As probes for the detection of the rearranged Ig gene loci of the variable regions of L-/H-chains, DNA fragments of known nucleotide sequences of adjacent conserved variable or constant regions are selected which constitute the Ig loci of the L-/H-chain in the mammal from which the DNA is derived, e.g. Balb/c mice. The utilization of murine DNA probes for the detection of human DNA sequences is based on sequence homologies between the murine and human DNAs. The DNA probe is isolated from suitable tissue of an appropriate mammal, e.g. Balb/c mouse liver, purified by molecular cloning in bacteriophage λ and subcloning appropriate DNA fragments in suitable plasmid vectors, such as pUC12 or pUC13, and recovering/purifying cloned DNA inserts using standard procedures. The purified probe DNA is labelled, e.g. radioactively-labelled by the well-known nick-translation technique, then hybridized with the human DNA library in buffer and salt solutions containing adjuncts, e.g. calcium chelators, viscosity regulating compounds, proteins, non-specific DNA and the like, at temperatures favoring selective hybridization.

Once a fragment has been identified which contains the desired DNA sequence, this fragment may be further manipulated to remove nonessential DNA, modified at one or both termini, and treated to remove all or a portion of intervening sequences, or the like.

The joining of the various DNA fragments in order to produce chimeric genes is performed in accordance with conventional techniques, for example, by blunt- or staggered-end ligation, restriction enzyme digestion to provide for appropriate cohesive termini, filling in cohesive ends as appropriate, alkaline phosphatase treatment to avoid undesirable joining, and ligation with appropriate ligases.

The transfer of the recombinant DNAs, e.g. the transfer of hybrid vectors, and the selection of transformed cells is described below.

Moreover, the invention relates to host cells transformed with the recombinant DNAs described above, namely host cells which are transformed with a DNA encoding the light chain and/or a DNA encoding the heavy chain of the desired chimeric antibody.

The host cells of the present invention have to be capable of culture in vitro and have to be of higher eukaryotic origin to provide a suitable environment for the production of active antibodies, since the biosynthesis of functional tetrameric antibody molecules requires correct nascent polypeptide chain folding, glycosylation, and assembly. Examples of suitable host cells according to the invention are mammalian cells, e.g. COS-7 cells, Bowes melanoma cells, chinese hamster ovary (CHO) cells, embryonic lung cells L-132, and in particular mammalian cells of lymphoid origin, such as myeloma or lymphoma cells, for example Sp2/0 cells. Sp2/0 (ATCC CRL 1581) is a well-characterized, Ig non-secreting mouse cell line, derived from the fusion of mouse spleen cells with the myeloma X63-Ag8. These host cells are transfected with the chimeric H-chain gene construct alone, with the L-chain gene construct alone, or with both, either transferred with the help of two separate vectors or by using a double-construct (L-chain/H-chain) vector as indicated hereinbefore. Particularly preferred are host cells transfected with both gene constructs, which are transferred with the help of two separate vectors, secreting chimeric monoclonal antibodies with an affinity to CEA as described hereinbefore, for example cells of the cell line EFVIII/γ4Na 75-75/CκGa5-6 (referred to as CE75-5-6). Also particularly preferred are host cells transfected with both gene constructs, which are simultaneously transferred with the help of a double-construct vector, secreting chimeric monoclonal antibodies of the invention, for example cells of the cell line EFIX-pCEA-Ig-(γ4;Cκ) (referred to as CE 4-8-13). Further examples of host cells of the invention are cells transfected with similar recombinant plasmids which contain alternative orientations of the H- and L-chain gene constructs, incorporating additional DNA elements to facilitate high levels of expression of the chimeric monoclonal antibodies.

The host cells of the invention are genetically stable, secrete chimeric monoclonal antibodies of the invention of constant specificity and can be activated from deep-frozen cultures by thawing and recloning.

The invention also relates to processes for the preparation of host cells secreting chimeric monoclonal antibodies with specificity to CEA as described hereinbefore, characterized in that a suitable cell is transformed with one or two vectors, e.g. by electroporation, calcium treatment, microinjection or protoplast fusion.

Vectors are introduced into mammalian cells by transfection in the presence of helper compounds, e.g. diethylaminoethyldextran, dimethyl sulfoxide, glycerol, polyethylene glycol or the like, or as co-precipitates of vector DNA and calcium phosphate. Further suitable methods include direct microinjection of vector DNA into the cell nucleus, protoplast fusion and electroporation, i.e. introduction of DNA by a short electrical pulse which transiently increases the permeability of cell membranes. The subsequent selection of transfected cells can be done using a selection marker which is either covalently integrated into the expression vector or added as a separate entity. Selection markers include genes which confer resistance to an tibiotics, e.g. G-418 (geneticin, a neomycin-derivative) or hygromycin, or genes which complement a genetic lesion of the host cell such as the absence of thymidine kinase, hypoxanthine phosphoribosyl transferase, dihydrofolate reductase, or the like.

The chimeric monoclonal antibodies and derivatives thereof according to the invention are used in a number of applications, especially for the diagnosis and therapy of cancer.

An example of diagnostic use is the qualitative and quantitative determination of human carcinoembryonic antigen, especially in biological fluids. The chimeric monoclonal antibodies and derivatives thereof may be used in any of the immunoassays known per se that utilize the binding interactions between antigen and monoclonal antibody, such as radioimmunoassays (RIA), enzyme-linked immunoassays, immunofluorescence tests, latex agglutination or haemagglutination.

Any of the known modifications of a RIA can be used, for example RIA in homogeneous phase, solid phase RIA or heterogeneous RIA, single RIA or double (sandwich) RIA with direct or indirect (competitive) determination of CEA. There is preferred a sandwich RIA in which a suitable carrier, for example the plastics surface of a microtitre plate or of a test tube, for example of polystyrene, polypropylene or polyvinyl chloride, glass or plastics beads, filter paper, or dextran, cellulose acetate or nitrocellulose sheets or the like, is coated with an antibody to CEA by simple adsorption or optionally after activation of the carrier, for example with glutaraldehyde or cyanogen bromide, and incubated with the test solution and a solution of an antibody radioactively labelled with $^{125}$I, the dissolved antibody recognizing another epitope of CEA than the carrier-bound antibody, and the amount of CEA is determined by measuring the radioactivity bound to the carrier. One of the two antibodies used in the sandwich RIA is a chimeric monoclonal antibody of the invention, the other one can be a known monoclonal or polyclonal anti-CEA antibody or also a chimeric antibody according to the invention.

The chimeric monoclonal antibodies according to the invention can be used as such or in the form of enzyme-conjugated derivatives in an enzyme-immunoassay. Such immunoassays include test procedures in which enzyme-labelled chimeric monoclonal antibody derivatives according to the invention or enzyme-labelled antibodies known per se that recognize and bind an epitope of the antibodies according to the invention are used. The amount of antigen is determined in a cascade-antigen-antibody-complex with the help of an enzymatic test.

There is preferred an ELISA (enzyme-linked immunosorbent assay) in which a carrier as described above for a RIA is coated with an anti-CEA antibody and incubated with a test solution containing CEA. After binding of CEA, a second antibody directed against CEA is added which binds to the antibody-antigen-complex. The bound antibodies are developed by a third enzyme-labelled antibody specific for the constant region of the second antibody. The amount of CEA is determined by an enzyme-substrate reaction. One of the antibodies used in the test is a chimeric monoclonal antibody of the invention, the other one can be a known monoclonal or polyclonal anti-CEA antibody or also a chimeric antibody according to the invention. The labelled antibody is, for example, an alkaline phosphatase-labelled goat-anti-human IgG antibody.

There is also preferred an ELISA in which a carrier coated with an antibody is incubated with a test solution containing CEA and with a solution of an antibody that is conjugated with an enzyme, the dissolved antibody recognizing a different CEA-epitope than does the carrier-bound antibody. One of the antibodies used in the test is a chimeric monoclonal antibody of the invention, the other one is a known monoclonal or polyclonal anti-CEA antibody.

The invention relates also to test kits for the determination of human CEA containing chimeric monoclonal antibodies to human CEA and/or derivatives thereof and, optionally, adjuncts.

Test kits according to the invention for a radioimmunoassay contain, for example, a suitable carrier, optionally freeze-dried or concentrated solutions of one or more monoclonal antibodies, solutions of a radioactively labelled monoclonal antibody or of radioactively labelled human CEA, standard solutions of human CEA, buffer solutions and, optionally, detergents for preventing non-specific adsorption and aggregate formation, pipettes, reaction vessels, calibration curves and the like. One or more of the monoclonal antibodies of the test kit are chimeric monoclonal antibodies of the invention.

Test kits according to the invention for an enzyme-immunoassay contain, for example, a suitable carrier, optionally freeze-dried or concentrated solutions of one or more monoclonal antibodies, optionally freeze-dried or concentrated solutions of an enzyme-labelled monoclonal antibody, of enzyme-labelled human CEA, of a polyclonal anti-human CEA serum and/or of enzyme-labelled monoclonal or polyclonal antibodies that recognize and bind the anti-human CEA antibody, enzyme substrates in solid or dissolved form, standard solutions of human CEA, buffer solutions, detergents, pipettes, reaction vessels, calibration curves, color scale tables and the like. One or more of the monoclonal antibodies of the test kit are chimeric monoclonal antibodies of the invention.

In addition, based on their reduced immunogenicity, the chimeric monoclonal antibodies and their derivatives are useful in therapy, for passive immunization without negative immune reactions such as serum sickness or anaphylactic shock, for localization and in vivo imaging of tumors, for specific treatment of diseased cells, e.g. site-directed delivery of cytotoxins, immuno-modulators or other pharmaceutically active molecules where local concentration of the active agent is an important factor, or the like. For in vivo imaging, the chimeric antibody is radiolabelled or conjugated with a metal chelate complexed with a radionuclide, e.g. iodine, yttrium, technetium, or the like, and radioscanning techniques may be used to detect primary and metastatic tumors. To that end, the radioactive antibody is injected e.g. intravenously and the patient scanned with a gamma imager at regular intervals. Tumors expressing CEA will take up more radioactive antibodies than other tissue and will be clearly recognized by the gamma imaging camera. Preferentially monoclonal antibodies labelled with $^{131}I$ are used for radioscanning in amounts of 3 to 8 µg representing 15 to 30 µCi per kg body weight. For biocidal activity in the treatment of cancer, the chimeric antibodies are used as derivatives conjugated to cytostatic or cytotoxic substances as described hereinbefore, e.g. ricin A, as radiolabelled derivatives, or else delivered in liposomes containing biocidal reagents. The therapeutic dose for mammals is between approximately 1 mg and 5 mg per kg body weight for monoclonal antibodies themselves, and between 0.1 mg and 5 mg per kg body weight for conjugates with cytotoxic drugs, depending on the status of the patient and the mode of application. Alternatively, the chimeric antibodies can be used in combination with components of the host immune system, e.g. complement, due to the presence of the native constant region. In vitro, the subject chimeric antibodies can be used in conjunction with complement to remove particular CEA-presenting cells from a mixture of cells.

The invention also relates to pharmaceutical preparations containing a chimeric monoclonal antibody or derivatives thereof with a high specificity for CEA as disclosed hereinbefore. The pharmaceutical preparations contain, for example, chimeric monoclonal antibodies or derivatives thereof in an effective amount together or in admixture with inorganic or organic, solid or liquid pharmaceutically acceptable carriers.

Preferred are pharmaceutical preparations for parenteral application. Preparations for intramuscular, subcutaneous or intravenous application are e.g. isotonic aqueous solutions or suspensions, optionally prepared shortly before use from lyophilized or concentrated preparations. The pharmaceutical preparations may be sterilized and contain adjuvants e.g. for conserving, stabilizing, wetting, emulsifying or solubilizing the ingredients, salts for the regulation of the osmotic pressure, buffer and/or compounds regulating the viscosity, e.g. sodium carboxycellulose, dextran, polyvinylpyrrolidone or gelatine. They are prepared by methods known in the art, e.g. by conventional mixing, dissolving or lyophilizing, and contain from approximately 0.01% to approximately 50% of active ingredients. The preparations for injections are processed, filled into ampoules or vials, and sealed under aseptic conditions according to methods known in the art.

The following examples illustrate the invention but do not limit it to any extent.

Figure Legends

Symbols for restriction sites: A—AluI, B—BamHI, Bg—BglII, E—EcoRI, H—HindIII, Hh—HhaI, P—PstI, Sa—SalI, Sp—SphI, X—XbaI, Xm—XmnI V: variable region Ig gene segment
J: joining segment
D: diversity segment
L: leader sequence Boxes indicate the position of the rearranged V-region and its leader peptide coding segment (black boxes), and the position of J-segments (open boxes).

FIG. 1A–1B:

(A) G: germline configuration of the mouse L-chain Ig gene locus showing the position of J-segments and the origin of the J-region probe L2 and L2.5: restriction maps of the CE 25 hybridoma-specific rearranged L-chain Ig genes deduced from Southern blot analysis (Example 3)

plasmid pCEA-L2a: cloned segment of the L2 gene (B) G: germline configuration of the mouse H-chain Ig gene locus showing the position of J-segments and the origin of the J-region probe H2 and H8: restriction maps of the CE 25 hybridoma-specific rearranged H-chain Ig genes deduced from Southern blot analysis (Example 3)

The plasmid pH8a1 is not shown, but it is constructed in an analogous manner to pCEA-L2a and contains the XbaI/XbaI segment of the H8 gene.

[E]: EcoRI sites in the cloned H8 gene that cannot be detected by Southern blot analysis of CE 25 hybridoma DNA

FIG. 2A–2B:

Detection of L2- and H8-specific mRNA transcripts in CE 25 hybridoma cells by Northern blot analysis (Example 6):

RNA blots of 25 and 50 µg of P3-NS2/1Ag4-cell RNA (NS) and CE 25 hybridoma-cell RNA (CE 25)

(a) using an L2 L-chain gene segment
(b) using an H8 H-chain gene segment.

FIG. 3:

Scheme for construction of the chimeric mouse/human L-chain gene pCEA-CκGa (Examples 8.1 and 8.2)

Symbols: see above.

FIG. 4:

Scheme for construction of the chimeric mouse/human H-chain gene pCEA-γ4Na (Examples 8.3 and 8.4)

Symbols: see above.

FIG. 5:

Scheme for the construction of pM1HuCκ-1a (Examples 10.1 and 10.2)

Symbols: see above; restriction sites placed in brackets are eliminated during the various cloning procedures.

FIG. 6:

Scheme for the construction of the chimeric double-construct pCEA(H+L)2neo holding both mouse/human (γ4;κ) anti-CEA, H- and L-chain Ig genes Symbols: see above; restriction sites placed in brackets are eliminated during the various cloning procedures.

FIG. 7:

Binding of the chimeric monoclonal antibody secretd by CE 4-8-13 to CEA OD: optical density.

| Abbreviations | |
|---|---|
| bp | base pairs |
| CDR | complementarity determining region |
| ddNTP | dideoxyribonucleotide triphosphate |
| | (N = adenine, cytosine, guanine or thymine) |
| dNTP | deoxyribonucleotide triphosphate |
| | (N = adenine, cytosine, guanine or thymine) |
| DMEM | Dulbeccos minimal essential medium |
| | (Dulbecco & Vogt, J. Exp. Med. 99, 167, 1954) |

-continued

| Abbreviations | |
|---|---|
| DTT | dithiothreitol |
| EDTA | ethylenediaminetetraacetic acid |
| FCS | foetal calf serum |
| HEPES | N-2-hydroxyethyl piperazine-N'-2' ethane sulphonic acid |
| HAT | hypoxanthine/aminopterin/thymidine |
| HT | hypoxanthine/thymidine |
| Ig | immunoglobulin |
| kb | kilobase (pairs) |
| MOPS | γ-morpholino propanesulphonic acid |
| NZ-amine | NZ-amine (10 g/l); NaCl (5 g/l); yeast extract (5 g/l, Difco); casamino acids (1 g/l, Difco) $MgSO_4 \cdot 7H_2O$ (2 g/l), pH 7.5 with NaOH |
| PBS | phosphate buffered saline (Dulbecco & Vogt, J. Exp. Med. 99, 167, 1954) |
| PBS-CM | PBS without $MgCl_2$ and $CaCl_2$ |
| RIA | radioimmunoassay |
| SDS | sodium dodecylsulphate |
| 20 × SET | 3 M NaCl, 20 mM EDTA, 0.4 M Tris-HCl, pH 7.8 |
| SSC | 0.15 M NaCl, 0.015M sodium citrate |
| TE buffer | 1 mM EDTA, 10 mM Tris-HCl, pH 8. |
| Tris | Tris (hydroxymethyl)aminomethane |

EXAMPLE 1
Preparation of Hybridoma Cell Line CE 25
1.1 Purification of Carcinoembryonic Antigen (CEA)

Colon carcinoma liver metastases obtained from autopsies (within 6 h of death) are extracted with saline. 1 vol. of tissue is first homogenized in 3 vol. of 0.02M phosphate buffer pH 7.4 at 4° C. for 10 min in a Sorvall Omnimixer at 8,000 rpm. The crude homogenate is then centrifuged at 8,000 g for 15 min at 4° C. The clear supernatant is applied to an immunoadsorbent consisting of a pool of the known anti-CEA monoclonal antibodies MAb 35 and MAb 115 (Haskell et al., Cancer Res. 43, 3857, 1983; Buchegger et al., J. Exp. Med. 158, 413, 1983) and MAb 73 (Buchegger et al., Immunol. Letters 5, 85, 1982) coupled to CNBr-activated Sepharose. CEA is eluted with 2M ammonium thiocyanate.

1.2 Immunization of Balb/c Mice

Balb/c mice two months of age are immunized with CEA by injecting intraperitoneally 15 μg of saline-extracted purified CEA with complete Freund's adjuvant. After 4 months, a series of booster injections comprising 15, 50 and 150 μg of the same saline CEA preparation without Freund's adjuvant given intraperitoneally 5, 4 and 3 days before fusion, respectively.

1.3 Cell Fusion

Cell fusion is accomplished using $1.5 \times 10^8$ spleen cells of immunized mice and $1.5 \times 10^7$ cells from the mouse myeloma P3-NS2/1Ag4 according to conventional previously described methods (Koehler & Milstein, Nature 256, 495, 1975). After washing, the cells are resuspended in 48 ml of standard Dulbecco's minimum essential medium (Gibco No. 0422501). $3 \times 10^6$ normal mouse peritoneal exudate cells per fusion are added as feeder cells. The cells are distributed into 96×0.5 ml Costar wells and fed 3 times per week with standard HAT selection medium for 3–6 weeks. When the growth of hybridoma cells becomes visible, the supernatants are screened as described in Example 1.4. Positive hybridomas, for example the cell line CE25 described in Example 1.5, are recloned and stored.

1.4 Antibody Detection in Hybridoma Supernatants

Culture fluids of growing hybridomas are tested for the presence of anti-CEA antibody by a modification of the assay of Farr (J. Infect. Dis. 103, 239, 1958) as described previously (Accolla et al., Proc. Natl. Acad. Sci. 77, 563, 1980). 1:10 (v/v) dilutions of cell culture supernatants are incubated in duplicate with $^{125}$I-labelled CEA in 0.02M Tris-HCl buffer, pH 7.4. CEA bound to antibodies is precipitated at 4° C. by adding cold, saturated ammonium sulphate solution in the presence of normal human serum.

1.5 Hybridoma Storage and Processing

Hybridoma CE 25 secreting anti-CEA antibody MAb CE 25 can be grown in culture, frozen at −80° C. or in liquid nitrogen and recultivated. The cells are cloned by the method of limiting dilution and expanded by forming ascites in Balb/c mice primed with pristane. Cell line CE 25 was deposited at the "Collection Nationale de Cultures de Microorganismes" of the Institut Pasteur, Paris, on Dec. 15, 1987, under the number I-719.

EXAMPLE 2
Isolation of DNA from the Hybridoma Cell Lines CE 25, P3-NS2/1Ag4 and Balb/c Mouse Kidney Cells CE 25 hybridoma cells ($5 \times 10^7$) are grown in suspension culture at 37° C. in DMEM (Seromed)+10% FCS (Seromed), 1 mM sodium pyruvate (Seromed), 2 mM glutamine (Seromed), 50 μM 2 mercaptoethanol and 100 μg/ml of gentamycin (Seromed) in a humidified atmosphere of air and 7.5% $CO_2$, in 175 cm$^3$ tissue culture flasks (Falcon 3028). Cells are harvested by centrifugation, flash-frozen in liquid nitrogen and kept frozen as a pellet at −80° C. in a clean, sterile plastic capped tube.

The frozen cells are resuspended in 10 ml of PBS to which is added 90 ml of 0.3 M sucrose, 5 mM $MgCl_2$, 0.1% (w/v) Triton-X100, 10 mM Tris-HCl, pH 7.5, at 4° C. in a clean, sterile 100 ml plastic beaker. Cells are lysed by mixing, and nuclei collected by centrifugation (10 min, 10,000 rpm, 4° C., Sorvall RC-5 centrifuge, SS-34 rotor). The supernatant is removed and the nuclear pellet resuspended in 4.5 ml of 75 mM NaCl, 24 mM EDTA, pH 8.0. Distilled water (100 μl), SDS (250 μl of a 10% (w/v) solution in distilled water), and 100 μl of proteinase K solution (Boehringer; 10 mg/ml solution-in distilled water) are added and mixed gently. The mixture is incubated at 37° C. overnight.

The solution is extracted by mixing with an equal volume of redistilled phenol saturated with 20 mM Tris-HCl, pH 8.0, at 0° C. The aqueous phase is recovered after centrifugation (10,000 rpm, room temperature, Sorvall RC-5 Centrifuge, SS-34 Rotor) and extracted twice with an equal volume of $CHCl_3$/isoamyl alcohol (24:1, v/v). DNA is precipitated by the addition of one-tenth volume of 3M NaOAc, pH 5.0, followed by two volumes of absolute ethanol at room temperature. The precipitated DNA is lifted from the ethanolic solution, placed in 1 ml of TE buffer and dissolved overnight at 4° C. The yield of DNA is approximately 0.5 mg.

DNA from cell line P3-NS2/1Ag4 is obtained likewise.

For preparations of DNA from Balb/c mouse kidney tissue, fresh mouse kidney is flash-frozen in liquid nitrogen, ground to a fine powder in a clean, sterile pestle and mortar in the presence of liquid nitrogen, and DNA extracted from an amount of tissue equivalent to $5 \times 10^7$ cells, following the procedure described above.

EXAMPLE 3
Analysis of Rearranged Ig H- and L-chain Gene Loci in CE 25 Cells

Hybridoma CE 25 contains H- and L-chain Ig gene loci derived from the P3-NS2/1Ag4 cell used as fusion partner for the generation of the hybridoma. The P3-NS2/1Ag4 cell line is derived from the MOPC-21 myeloma (Storb et al., Nucleic Acids Res. 8, 4681, 1980). These 'endogenous' rearranged loci are distinguished from CE 25-specific rearranged genes by the following procedures:

3.1 Source and Preparation of Probe DNA Fragments

The probe DNA segment used for the detection of the Balb/c mouse germline H-chain J-region DNA segment is an approximately 1750 bp BglII/XbaI segment of Balb/c mouse liver DNA, corresponding to nucleotide positions 1130–2881 of the published germline H-chain Ig locus (Newell et al., Science 209, 1128, 1980; EMBL data base entry MUSIGCDO7).

The probe DNA segment used for the detection of the Balb/c mouse germline L-chain J-region segment is an approximately 2240 bp HindIII/XbaI segment of Balb/c mouse liver DNA, corresponding to nucleotide positions 659–2900 of the published germline L-chain Ig locus (Max et al., Proc. Natl. Acad. Sci. 76, 3450, 3454, 1979; EMBL data base sequence entry MUSIGKJC2).

DNA probes are purified by molecular cloning of Balb/c mouse liver DNA in bacteriophage λ, subcloning appropriate DNA fragments in pUC12- or pUC13-plasmid vectors, and recovering/purifying cloned DNA inserts using standard procedures (Maniatis et al., "Molecular Cloning: A laboratory manual", Cold Spr. Harbor, N.Y., 1982).

DNA probes are prepared from 300 ng of purified DNA fragments by nicktranslation in the presence of $\alpha$-$^{32}$P-dCTP, *E. coli* DNA polymerase-I and DNaseI, using the standard published procedure (Rigby et al., J. Mol. Biol. 113, 237, 1977). Labelled probe DNA is separated from unincorporated label using Sephadex G50 (Pharmacia) chromatography with a 10×0.5 cm separation column and an elution buffer containing 150 mM NaCl, 10 mM EDTA, 0.1% (w/v) SDS, 50 mM Tris-HCl, pH 7.5.

3.2 Gel Electrophoresis of DNA

Samples of DNA (5 μg) from (a) the P3-NS2/1-Ag4 myeloma used as parental fusion partner in the generation of the CE 25 hybridoma, (b) the CE 25 hybridoma, and (c) Balb/c mouse kidney cells, prepared as described in Example 2, are digested to completion using the restriction enzymes XbaI, BglII, EcoRI+HindIII, BamHI, EcoRI or HindIII (Boehringer) under conditions recommended by the manufacturer. DNA fragments are separated by flat-bed agarose gel electrophoresis using 10×20×0.5 cm 0.5% (w/v) agarose (Biorad, standard low $M_r$) gels and electrophoresis buffer containing 25 mM disodium-EDTA, 90 mM Tris-base, 90 mM boric acid, pH 8.3. Fragments of bacteriophage λ digested either with HindIII or with EcoRI are pooled and radioactively labelled using Klenow DNA polymerase I fragment (Boehringer) in the presence of dNTPs and $\alpha$-$^{32}$P-dNTPs using a published procedure (Maniatis et al., "Molecular Cloning: A laboratory manual", Cold Spr. Harbor, N.Y., 1982). These are included in separate lanes of the agarose gel to provide a range of labelled DNA marker fragments of known size. After separation of DNA fragments by electrophoresis they are transferred by blotting at room temperature to nitrocellulose membrane using the published Southern procedure (Southern, J. Mol. Biol. 98, 503, 1975) with some minor modifications as follows. After electrophoresis excess agarose is trimmed from the edges of the gel, after which it is soaked at room temperature in 500 ml of 0.25M HCl solution for 30 min, followed by soaking in 500 ml of 1.5M NaCl, 0.5M NaOH for 60 min to denature the DNA. The gel is rinsed briefly with distilled water and then soaked for 60 min in neutralising solution (3M NaCl, 0.3M Tris-HCl, pH 7.5). DNA fragments are then transferred overnight to a nitrocellulose membrane (Schleicher & Schuell, 0.45 μm pore size) by the published procedure referred to above using a solution containing 3M NaCl, 0.3M sodium citrate, pH 6.8. The nitrocellulose membrane containing the blotted DNA fragments is air-dried and baked at 80° C. for 2 h under vacuum. After baking, excess dried salts are removed by soaking the membrane in 0.75M NaCl, 0.075M sodium citrate, pH 6.8, before hybridizing with radioactively-labelled DNA probes.

3.3 DNA Hybridization

Nitrocellulose filters prepared as described in Example 3.2 are prehybridized in heat-sealed plastic bags for 4 h at 65° C. in 20 ml of prehybridization solution containing 0.2 ml of 10% (w/v) SDS, 0.4 ml of 5% (w/v) sodium pyrophosphate, 0.4 ml of herring sperm DNA (5 mg/ml in distilled water) sheared by passage through an 18 gauge hypodermic needle, 5 ml of Denhardt's solution (Denhardt, BBRC 23, 641, 1966; 0.2% (w/v) bovine serum albumin, 0.02% (w/v) polyvinylpyrrolidone, 0.02% (w/v) Ficoll-400 in 20×SET buffer (3M NaCl, 20 mM EDTA, 0.4M Tris-HCl, pH 7.8)) and 14 ml of distilled water.

The DNA hybridization mixture contains $10^7$ cpm of radioactively-labelled DNA probe, 10 ml of prehybridization solution, prepared as described above, and 10% (w/v) dextran sulphate (Sigma). The mixture is heated at 100° C. for 20 min to denature the DNA. For hybridization, the prehybridization mixture is removed from the plastic bag and replaced by the hybridization mixture. After excluding air-bubbles the bag is resealed and incubated overnight at 65° C. To remove non-specifically bound DNA from the membrane, the hybridization mixture and membrane are removed from the plastic bag. The membrane is placed in a bath containing 500 ml of 5×SSC, 0.1% (w/v) sodium pyrophosphate and washed for 15 min at 65° C. The membrane is then washed sequentially at 65° C. for 30 min in 500 ml of solution containing 4×SSC, 3×SSC, 2×SSC and finally 1×SSC, all containing 0.1% (w/v) sodium pyrophosphate. The membrane is air-dried, sealed in a clean, thin polythene bag, and autoradiographed at −70° C. using Kodak X-ray film (X-omat TM AR) and image intensifying screens, for up to three days.

The results are summarized in Table 1 below and illustrated in FIG. 1:

TABLE 1

Size of CE 25 hybridoma-specific genomic DNA fragments showing homology with murine H-chain and L-chain Ig J-region DNA probes

| DNA probe | restriction enzyme used/size of fragments in kb | | | | | |
|---|---|---|---|---|---|---|
|  | XbaI | BlII | EcoRI/HindIII | BamHI | EcoRI | HindIII |
| H-chain | 8.0* | 21.0 | 5.6 | 10.8 | 7.5 | 6.3 |
|  | 2.1 | 20.0 | 2.1 | 8.3 | 2.5 | 2.9 |
| L-chain | 2.5 | 1.8 | 2.1 | 6.4 | 20.0 | 9.5 |
|  | 2.0* | 1.2 | 1.9 | 4.5 | 18.0 | 1.9 |

*fragments encoding functional H- and L-chain V-region H8 and L2 segments of the CE 25 antibody By comparison with the parental fusion partner cell line P3-NS2/1Ag4, the CE 25 hybridoma contains two additional rearranged H-chain Ig gene loci and two additional rearranged L-chain Ig gene loci. These are referred to as H2 and H8 (FIG. 1B), and L2 and L2.5 (FIG. 1A), respectively, from the sizes of the mouse genomic DNA fragments detected in XbaI restriction digests by Southern blotting using mouse Ig-specific DNA probes.

EXAMPLE 4

Molecular Cloning of Functionally-rearranged H- and L-chain Ig Genes of the CE 25 Hybridoma 4.1 Preparation of Size-Selected DNA Fractions Containing CE 25 Hybridoma-specific Rearranged H- and L-chain Ig Loci CE 25 hybridoma DNA (50 μg) is digested to completion with XbaI, extracted with an equal volume of CHCl$_3$/redistilled phenol (1:1, v/v, saturated with 20 mM Tris-HCl, pH 8.0), followed by extraction with an equal volume of CHCl$_3$ to remove traces of phenol. DNA is precipitated by the addition of 0.1 vol. of 3M NaOAc, pH 5.0 and 2.5 vol. of absolute ethanol at −20° C. The DNA pellet is recovered, dissolved in 150 μl of TE buffer and applied to a 12 ml, 5–24% (w/v) NaCl gradient in TE buffer in a polyallomer tube for the Beckman SW41 rotor. Gradients are centrifuged for 4.5 h at 37,000 rpm at 25° C., and fractionated from the bottom. DNA fractions (300 μl) corresponding to (a) 1.5–2.5 kb-long DNA fragments, and (b) 6.0–9.0 kb-long DNA fragments, are collected, pooled and precipitated using 2.5 vol. of absolute ethanol at −20° C. DNA from pooled fractions (a) and (b) are recovered by centrifugation, dried under vacuum and dissolved in TE buffer to concentrations of 50 ng/μl and 200 ng/μl, respectively.

4.2 DNA Ligations and Packaging into Bacteriophage Particles

DNA samples (1 μl) from fractions (a) and (b) as described above are ligated overnight at 4° C. with 0.8 μg of λ-OngC/XbaI-digested bacteriophage DNA arms (Stratagene Inc., San Diego, USA) in 5 μl of a solution containing 10 mM DTT, 1 mM ATP, 10 mM MgCl$_2$, 20 mM Tris-HCl, pH 7.6, in the presence of 5 units of T4 DNA ligase (Boehringer). Ligation mixtures are packaged using Gigapack 'PLUS' (Stratagene Inc., San Diego, USA) and plated on *E. coli* K12/VCS257 (prepared by growth on NZ-amin/0.4% (w/v) maltose) using NZ-amin growth medium, according to the manufacturer's instructions, at a density of approximately 250 pfu/cm$^2$ using standard microbiological procedures. Plates are incubated overnight at 37° C.

The L2 and L2.5 rearranged L-chain Ig gene loci are detected in library (a) by Benton & Davis hybridization screening (Science 196, 180, 1977) using the nick-translated $^{32}$P-labelled mouse L-chain Ig DNA probe described in Example 3.1. Positively-hybridizing plaques are plaquepurified, picked using the tip of a sterile pasteur pipette, and the phage resuspended in 1 ml of phage buffer (100 mM NaCl, 8 mM MgSO$_4$·7H$_2$O, 0.01% (w/v) gelatin, 5 mM Tris-HCl, pH 7.5). Phage lysates (10 ml) are prepared by adsorbing 20 μl of phage suspension to a 100 μl volume of cells taken from an overnight culture of *E. coli* K12/VCS257, grown in NZ-amin medium supplemented with 0.4% (w/v) maltose. The mixture is diluted to 10 ml with fresh NZ-amin medium in sterile 50 ml Falcon tubes and grown overnight at 37° C. with vigorous shaking. CHCl$_3$ (20 μl) is added and shaking continued at 37° C. for 30 min. Recombinant bacteriophage DNA is prepared from the lysates using a published procedure devised by Blattner et al. (Science 202, 1279, 1978). DNA obtained after the final ethanol precipitation step is dissolved in 100 μl of TE buffer. Yields of phage DNA are approximately 100 μg.

Samples of DNA (1 μg) from each positively-hybridizing recombinant bacteriophage are digested to completion using the restriction endonuclease XbaI. An L2 gene segment is identified as a 2 kb XbaI restriction fragment when the digested recombinant DNA samples are analysed by 1% (w/v) agarose gel electrophoresis. The approximately 2.0 kb L2 gene segment is cut from the agarose gel, purified by phenol/CHCl$_3$ extraction and recovered by ethanol precipitation. The purified DNA fragment is then subcloned in both orientations into the pUC12 plasmid cloning vector, linearized by XbaI digestion. All procedures are standard methods (Maniatis et al., "Molecular Cloning: A laboratory manual", Cold Spr. Harbor, N.Y., 1982). Restriction mapping of these plasmid subclones using the restriction endonucleases XbaI, BglII, PstI, HindIII and BamHI confirms that the structure of the cloned L2 gene segment corresponds to that of the original genomic L2 gene segment, deduced from Southern blotting of CE 25 hybridoma DNA as described in Example 3. Plasmids containing the cloned L2 gene segment in either orientation are designated pCEA-L2a and pCEA-L2b. A restriction map of pCEA-L2a is shown in FIG. 1A.

Figure 1B:
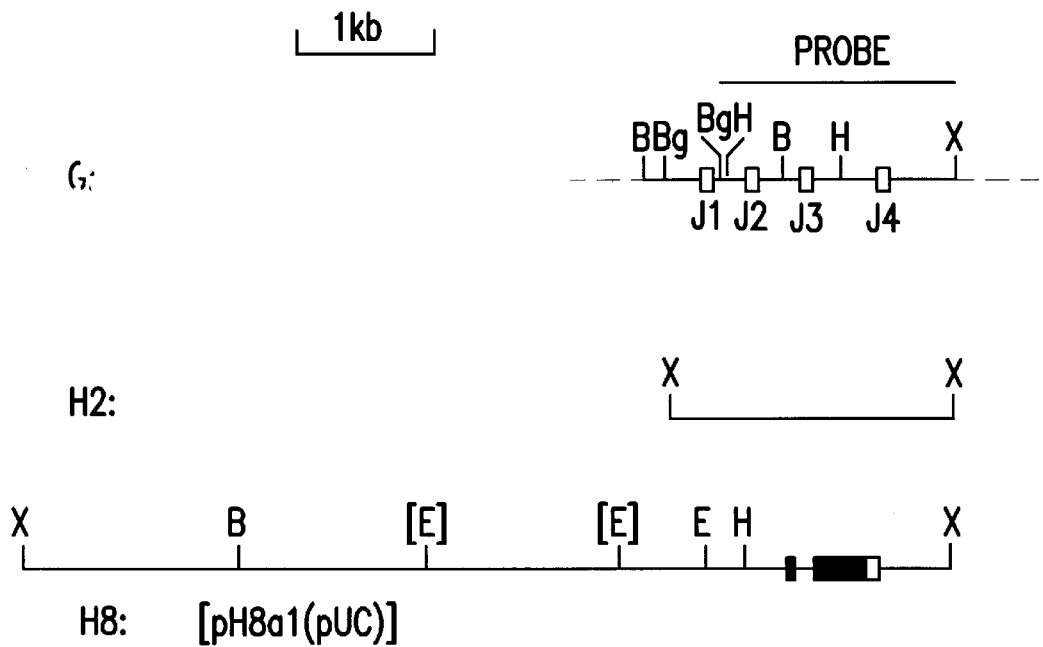

Library (b) is used as a source of the H8 rearranged H-chain Ig gene segment using the same procedure. Screening of recombinant phage for H-chain gene loci is achieved by hybridizing with the H-chain-specific radioactively-labelled DNA probe described in Example 3.1. Positively-hybridizing recombinant phages are plaque-purified, DNA is isolated and digested using XbaI as described above. An H8 gene sequence is identified as an approximately 8 kb restriction fragment when separated from cloning vector DNA by digestion with XbaI followed by 1% (w/v) agarose gel electrophoresis. The H8 gene is subcloned in both orientations into the plasmid vector pUC12, linearized by digestion using XbaI. Restriction mapping of the DNA subclones using the enzymes XbaI, PstI, HindIII and BamHI confirms that the structure of the cloned H8 gene segment corresponds to that of the genomic H8 rearranged H-chain Ig locus, deduced from Southern blotting of CE 25 hybridoma DNA using an H-chain-specific radioactively-labelled DNA probe as described in Example 3. These H8 DNA subclones are designated pH8a1 and pH8b1. A restriction map of the pH8a1 XbaI insert DNA fragment is shown in FIG. 1B.

4.3 Nucleotide Sequence Analysis of the L2 and H8 Gene Segments

Nucleotide sequencing of the L2 and H8 gene loci in pCEA-L2(a or b) and pH8(a1 or b1) is performed using the published Sanger dideoxynucleotide chain-termination method (Sanger et al., Proc. Natl. Acad. Sci. 74, 5463, 1977). Recombinant plasmid DNAs are cut using appropriate restriction endonucleases and DNA fragments to be sequenced recovered by 1% (w/v) gel electrophoresis. DNA fragments are then cloned and sequenced in M13 bacteriophage vectors with the Amersham M13 Cloning System, using the instructions supplied (Amersham International PLC, UK).

The L2 gene segment is sequenced from the 5'-XbaI restriction site to nucleotide 1395, located 3' to the rearranged L-chain V-J4 region. The nucleotide sequence is the one given in formula III.

This data confirms the restriction map of the cloned L2 gene in this region (FIG. 1A) and defines the sequence of the first exon encoding the N-terminal residues of the L-chain leader peptide (beginning with methionine at position 733 in the sequence), an intervening sequence (nucleotides 781–987), and the coding sequence of the remainder of the leader peptide and the rearranged L2 V-region ending in a proline residue located at the V-J4 region (nucleotides 988–1284). Nucleotides 1285–1395 correspond to the known mouse κ-chain Ig germline sequence (between 1725–1836 of the EMBL data bank sequence entry MUSIGKJC2). Nucleotides 680–1284 correspond to a known mouse germline L-chain V-region (L7, Pech et al., Nature 291, 668, 1981) except for 7 changes in the V-region coding sequence, which may arise by somatic mutation. This data defines the amino acid coding sequence of the rearranged L2 L-chain gene encompassing the leader peptide, the three framework regions and complementarity determining regions CDRLs 1–3 (nucleotide residues 1069–1102, 1147–1167, 1263–1291) including the in-frame V-J4 junction.

The H8 H-chain gene segment is sequenced from the internal HindIII restriction site to nucleotide 857 located 3' to the rearranged H-chain V-D-J region. The nucleotide sequence is the one given in formula IV.

This data confirms the restriction map of this region of the H8 gene (FIG. 1B) and defines the sequence of the first exon encoding the N-terminal 16 amino acid residues of the leader peptide (beginning with methionine at position 322 in the sequence), an intervening sequence (nucleotides 368–473) and the coding sequence of the remainder of the leader peptide and the H8 V-region up to a serine residue (nucleotides 474–844). Nucleotide residues 797–857 correspond to the mouse H-chain Ig germline sequence (between 2291–2352 of the EMBL data bank sequence entry MUSIGCD007) except for three nucleotide changes which affect the predicted coding sequence of the J-region of the H-chain polypeptide. The first 796 nucleotide residues of the sequence are homologous to, but not identical to, known mouse H-chain V-region, as deduced from a search of the available sequence data in the Genbank, NBRF or EMBL libraries. This sequencing data defines the amino acid coding sequence encompassing the leader peptide, the three framework regions and CDRHs 1–3 (nucleotides 575–595, 629–680, 776–805), the origin of the H-chain diversity (D) segment (which originates either from DSP2.3, DSP2.4 or DSP2.6 of the mouse H-chain Ig germline locus) and the in-frame V-D-J4 junction of the rearranged H8 H-chain gene of hybridoma CE 25.

EXAMPLE 5

Comparison Between Nucleotide Sequences of Expressed H- and L-chain Ig mRNAs and Nucleotide Sequences of Rearranged H- and L-chain Genes from the Mouse Hybridoma CE 25

5.1 Extraction of Total Cellular RNA

Total RNA is extracted using the LiCl/urea method described by Auffray & Rougeon (Eur. J. Biochem. 107, 303, 1980) as modified by Le Meur et al. (Cell 23, 561, 1981). CE 25 hybridoma cells ($5 \times 10^7$) are grown and prepared as described in Example 2. Cell pellets are thawed directly in the tube in the presence of 5 ml of LiCl/urea (3 M LiCl, 6M urea, 200 µg/ml heparin, 0.1% SDS, 10 mM NaOAc, pH 5.0). Subsequent steps are described in the published procedures. The method yields approximately 50 µg of total cellular RNA. Final purified material is stored under 70% (v/v) ethanol at −80° C. at a known concentration.

5.2 Nucleotide Sequencing of Expressed H- and L-chain Ig mRNAs

Nucleotide sequencing of mRNA from the CE 25 hybridoma is accomplished directly in total cellular RNA preparations utilising specific radioactively-labelled oligonucleotide primers. These primer oligonucleotides are synthesized chemically using a published procedure (Rink et al., Nuc. Acids Res. 12, 6369, 1984).

(a) Sequencing of mouse Cκ-containing mRNA is achieved using a specific oligonucleotide primer of composition HO-5'-dGGGAAGATGGATACAGTTGG-3'-OH. This sequence is complementary to codons 3–12 of the published mouse Cκ coding sequence (Altenburger et al., Nuc. Acids Res. 9, 971, 1981).

(b) Sequencing of mouse IgG1-specific mRNA is achieved using a specific oligonucleotide primer of composition HO-5'-dGGCCAGTGGATAGAC-3'-OH. This sequence is complementary to codons 7–11 of the CH1 domain (first constant region exon) of the mouse Igγ1 H-chain coding sequence (Honjo et al., Proc. Natl. Acad. Sci. 18, 559, 1979).

Both oligonucleotides are radioactively-labelled at the 5'-end in the presence of $\gamma$-$^{32}$P-ATP (Amersham) using T4-polynucleotide kinase (Pharmacia), to a specific activity of $2 \times 10^6$ dpm/pmole. Labelling and separation of radioactively-labelled oligonucleotides from unincorporated $\gamma$-$^{32}$P-ATP using Sephadex G50 (Pharmacia) chromatography is carried out using a published procedure (Qu et al., Nuc. Acids Res. 11, 5903, 1983).

For sequencing, samples (25 µg) of stored RNA under ethanol are recovered by centrifugation at 4° C. for 30 min using an Eppendorf centrifuge, and resuspended in TE buffer containing $10^6$ dpm of 5'-end-labelled primer. This mixture is aliquoted into 5×1 ml Eppendorf tubes containing 1 µl of annealing buffer, 5 units of reverse transcriptase (Genofit SA, Geneva), 1 µl of dNTP mixture and 1 µl of either ddATP (200 µM), ddGTP (100 µM), ddCTP (80 µM) or ddTTP (200 µM) solution in distilled water in a final volume of 5 µl (all from Amersham International, UK). The fifth reaction tube contains no ddNTPs and is used to monitor the integrity of the mRNA. Reaction mixtures are incubated at 37° C. for 30 min for primer (a), or at 42° C. for 30 min for primer (b). Buffers and mixtures are as follows: annealing buffer for primer (a): 60 mM MgCl$_2$, 0.4 M KCl, 0.5 M Tris-HCl, pH 8.3; annealing buffer for primer (b): 60 mM MgCl$_2$, 0.6 M NaCl, 0.5 M Tris-HCl, pH 8.3; dNTP mixture: 2 mM concentration of each of dNTPs in distilled water, except for that corresponding to the ddNT-P used in the particular sequencing reaction, which is used at a concentration of 0.5 mM.

Sequencing reactions are stopped by the addition of 20 µl of distilled water and 30 µl of 0.6 M NaOH to each tube. RNA is hydrolysed by incubation overnight at 37° C. Reaction mixtures are neutralized by the addition of 8.4 µl of 3 M acetic acid, and DNA precipitated by addition of 2.5 vols. of absolute ethanol in the presence of 0.3 M NaOAc, pH 5.0. The DNA pellets are dried in air at 60° C. and resuspended in 2 µl of sequencing dye mixture and electrophoresed on 6% polyacrylamide/urea DNA sequencing gels using standard materials and procedures (Sanger et. al., Proc. Natl. Acad. Sci. 74, 5463, 1977).

The sequence of the L-chain mRNA specifically expressed in mouse hybridoma CE 25 is

```
                              1160              1180              1200
          ATGAAGTATGCTTCTGAGTCTATCTCTGGGATCCCTTCCAGGTTTAGTGGCAGTGGATCA
                                       |         |         |         |
mRNA:                          3'-GACCCTAGGGAAGGTCCAAATCACCGTCACCTAGT 1220              1240              1260
          GGGACAGATTTTACTCTTACCATCAATAGTGTGGAGTCTGAAGATATTGCAGATTATTAC
            |         |         |         |         |         |
mRNA:     CCCTGTCTAAAATGAGAATGGTAGTTATCACACCTCAGACTTCTATAACGTCTAATAATG
```

```
                           -continued
                   1280              1300               1320
         TGTCAACAAAGTCATGGCTGGCCATTCACGTTCGGCTCGGGGACAAAGTTGGAAATAAAA
              |                |                 |              |
mRNA:    ACAGTTGTTTCAGTACCGACCGGTAAGTGCAAGCCGAGCCCCTGTTTCAACCTTTATTTT

CG mRNA:    GCccgactacgacgtggttgacataggtagaagggg-5'
             |------------ primer --------------|
```

The sequence runs 3'–5' and is complementary to the portion of the cloned and sequenced L2 L-chain Ig gene isolated from CE 25 hybridoma DNA from nucleotide 1166-1322 (cf. Example 4.3).

The sequence of the H-chain mRNA specifically expressed in mouse hybridoma CE 25 is

```
                    614               634                654
         TCGCCAGACTCCAGAGAAGAGGCTGGAGTGGGTCACATCCATTAGTAGTGGTGGTACCAC
                       |                 |                  |          |
mRNA:                  3'-ACCTCACCCAGTGTAGGTAATCATCACCACCATGGTG 674               694                714
         CTACTATCCAGACAGTGTGAAGGGCCGATTCACCATCTCCAGAGATAATGCCAGGAACAT
              |         |         |          |          |         |
mRNA:    GATGATAGGTCTGTCACACTTCCCGGCTAAGTGGTAGAGGTCTCTATTACGGTCCTTGTA 734               754                774
         CCTGTACCTGCAAGTGAGCAGTCTGAGGTCTGAGGACACGGCCATTTATTACTGTGCAAG
              |         |         |          |          |         |
mRNA:    GGACATGGACGTTCACTCGTCAGACTCCAGACTCCTGTGCCGGTAAATAATGACACGTTC 794               814                834
         AGGTTTCTATGATGGTTACCTCTATGTTGTGGACTACTGGGGTCAAGGAACCTCACTCAC
              |         |         |          |          |         |
mRNA:    TCCAAAGATACTACCAATGGAGATACAACACCTGATGACCCCAGTTCCTTGGAGTGAGTG

854
         CGTCTCCTCAGGTAAGAATGGCC mRNA:    GCAGA-5'
```

The sequence runs 3'–5' and is complementary to the portion of the cloned and sequenced H8 H-chain Ig gene isolated from CE 25 hybridoma DNA from nucleotide 618-839 (cf. Example 4.3). It does not include the sequence complementary to the primer binding site.

EXAMPLE 6
Specific Transcription of L2- and H8-specific mRNA Transcripts in CE 25 Hybridoma Cells by Northern Blot Analysis Total cellular RNA from either CE 25 hybridoma cells or from P3-NS2/1Ag4 cells is prepared as described in Example 5. Samples of RNA (25 and 50 µg) are recovered by centrifugation from the ethanol used for storage, after which they are resuspended in 20 µl of solution containing 2.2 M formaldehyde, 50% (v/v) formamide, 1 mM EDTA, 40% (w/v) sucrose, 50 mM γ-morpholino propanesulphonic acid (MOPS) pH 7.0, and 0.5% (w/v) xylene cyanol and 0.5% (w/v) bromocresol green, used as marker dyes for monitoring the progress of electrophoresis. After mixing, samples are loaded on to 1% (w/v) agarose gels using an electrophoresis buffer containing 1 mM EDTA, 2.2 M formaldehyde, 50 mM MOPS, pH 7.0. Gels are pre-electrophoresed for 30 min before use.

Figure 3:
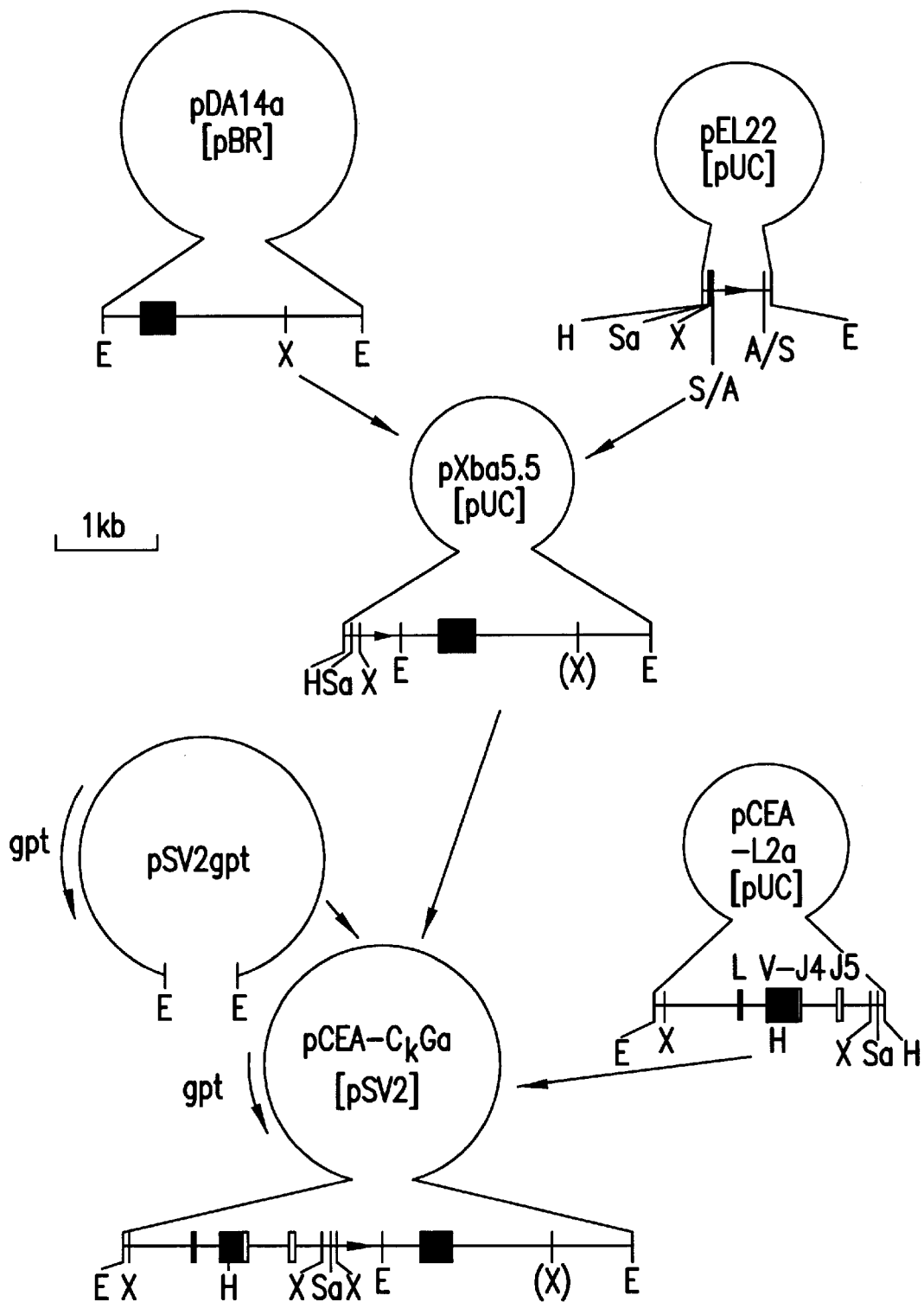

After electrophoresis, excess agarose is trimmed from the sides of the gel, which is then soaked in 20×SSC buffer for 5 min. RNA is transferred to nitrocellulose membrane by the standard Northern blot procedure (Maniatis et al., "Molecular Cloning: A laboratory manual", Cold Spr. Harbor, N.Y., 1982). After overnight transfer, the membrane is air-dried and baked for 2 h at 80° C. under vacuum. Before hybridization, the membrane is prehybridized in 20 ml of a solution containing 50% (v/v) formamide, 5×SSC buffer, 5×Denhardt's solution (described in Example 3.3), 10 mM EDTA, 0.1% (w/v) SDS, 50 mM sodium phosphate, pH 6.8 and 2 ml of sheared herring sperm DNA (5 mg/ml in distilled water, Example 3.3). Incubation is carried out in a heat-sealed plastic bag at 42° C. for 8 h. For hybridization, the prehybridization mixture is removed from the plastic bag and replaced with hybridization solution similar to prehybridization solution but containing 2×Denhardt's solution instead of 5×Denhardt's solution, and $2 \times 10^7$ cpm of nick-translated $^{32}$P-labelled denatured hybridization probe DNA. The radioactively-labelled DNA probe specific for the rearranged L2 Ig L-chain gene segment is the plasmid pCEA-L2a (FIG. 1A & FIG. 3). The radioactively-labelled DNA specific for the rearranged H8 H-chain gene segment is the plasmid pH8a1 (FIG. 1B). Preparation of nick-translated probe DNA is described in Example 3.1. After hybridization for 16 h at 42° C., the membrane is removed from the plastic bag and washed twice for 1 h at 42° C. in hybridization mixture without DNA probe, then once in 2×SSC, 0.1% (w/v) SDS also at 42° C., followed by two washes in 0.1×SSC, 0.1% (w/v) SDS, both at room temperature. The membrane is then air-dried, placed in a thin plastic bag and exposed to Kodak X-omat TM AR diagnostic film at –70° C. using an image intensifying screen.

Figure 2A:
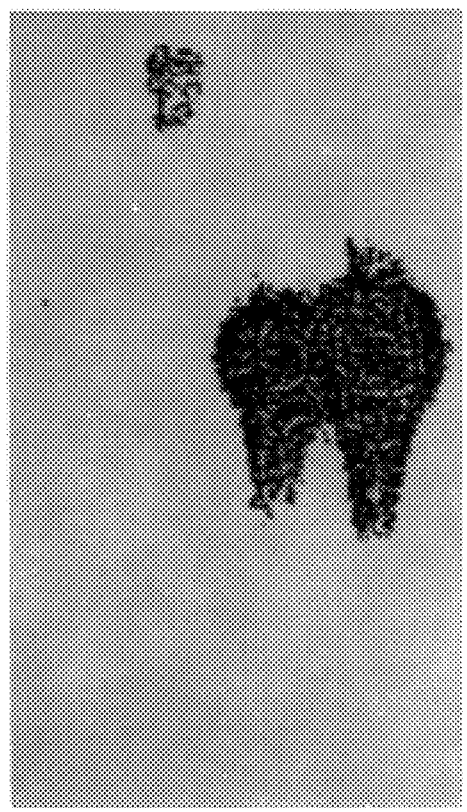
Figure 2B:

The results of the Northern blot analysis are shown in FIG. 2.

EXAMPLE 7
Molecular Cloning of Constant Region Segments of the Human Ig Gene Loci

7.1 Human DNA Library

A human DNA library is constructed in the bacteriophage λ vector Charon 4a, by limited digestion of human foetal liver DNA with restriction endonucleases HaeIII and AluI using published procedures (Lawn et al., Cell 15, 1157, 1978). Approximately $1 \times 10^6$ independent recombinant phages are plated on *E. coli* K12/803 and screened by nucleic acid hybridization for the presence of human Cκ L-chain sequences and for human Igγ4 H-chain sequences, as described below.

7.2 Isolation of Human Cκ-containing DNA Segment

A nick-translated $^{32}$-P-labelled mouse Ig L-chain DNA probe is prepared corresponding to that described in Example 3.1, and used to screen recombinant phage using the procedure described in Example 4.2. DNA is isolated from plaque-purified positively-hybridizing plaques using a standard published procedure (Blattner et al., Science 202, 1279, 1978). A 2.5 kb EcoRI DNA fragment encompassing the human Cκ coding segment (Hieter et al., J. Biol. Chem. 257, 1516, 1982) is isolated in this manner and subcloned in both orientations into the plasmid vector pBR322, linearized using EcoRI. These plasmids are referred to as pDA13b and pDA14a, respectively. A restriction map of pDA14a is constructed and is shown in FIG. 3.

7.3 Isolation of Human γ4 H-Chain-containing DNA Segment

Figure 4:
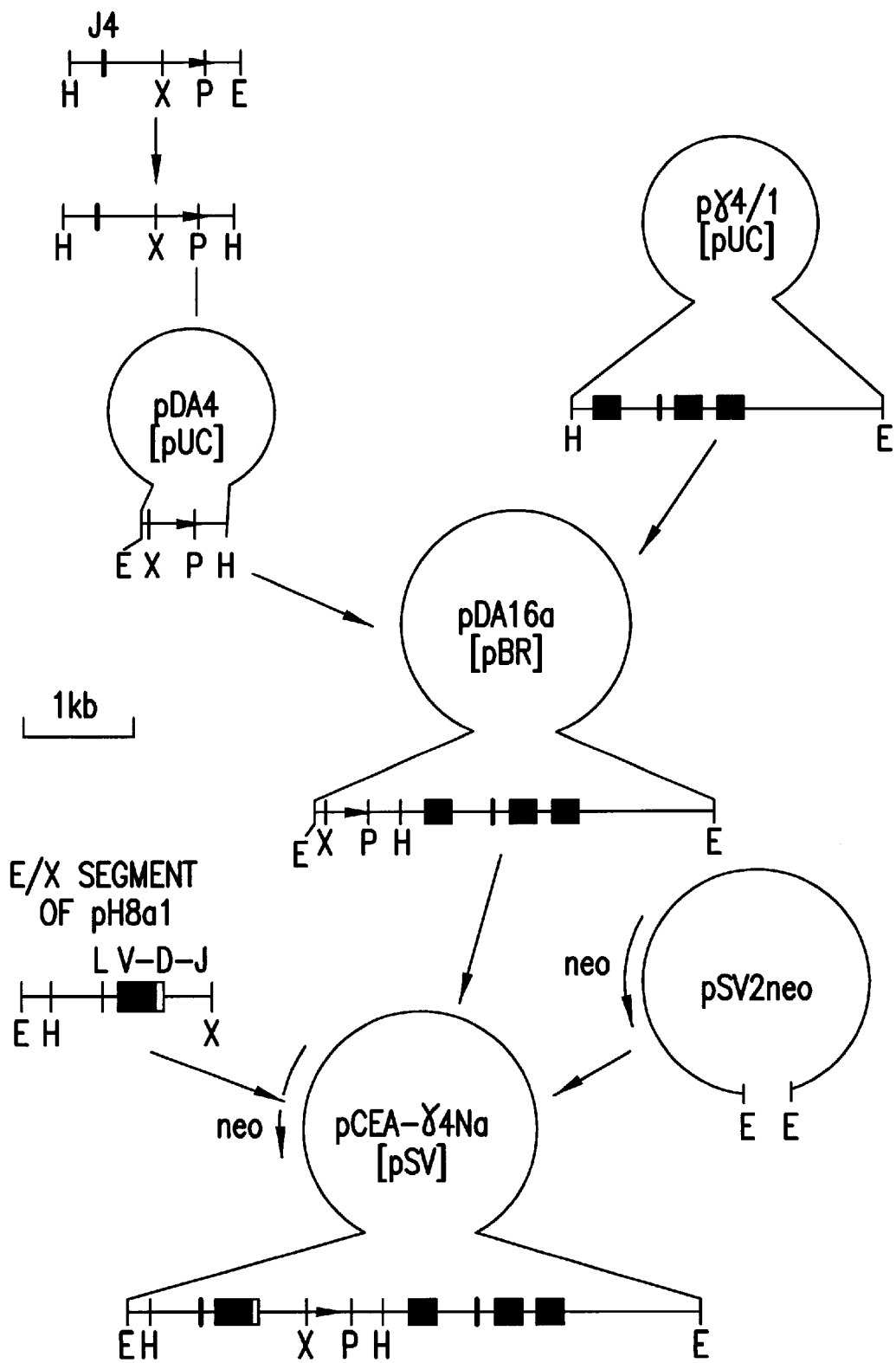

A nick-translated $^{32}$P-labelled mouse IgG H-chain DNA probe corresponding to the XbaI/HhaI fragment of the mouse γ2b gene locus is used to screen recombinant phage as described previously (Takahashi et al., Cell 29, 671, 1982). One DNA clone (#188) contains the human γ4 gene locus as determined by restriction mapping and by nucleotide sequence analysis using the Gilbert-Maxam procedure (Proc. Natl. Acad. Sci. 74, 560, 1977). The portion of clone #188 that is sequenced corresponds exactly to that of the published human γ4 gene between nucleotides 27–98 (EMBL data base sequence entry HUMIGCD2). An approximately 3 kb HindIII/EcoRI DNA restriction fragment, including the 4 exons of the γ4 gene locus, is subcloned into the plasmid vector pUC12 cleaved using HindIII/EcoRI. The plasmid is designated pγ4/1. The HindIII site in pγ4/1 is found in the γ4 gene locus of Balb/c mouse DNA (nucleotide position 1 of EMBL data base sequence entry HUMIGCD2; Ellison et al., DNA 1, 11, 1981). The EcoRI site is derived from the EcoRI cloning site in the Charon 4a bacteriophage lambda cloning vector at the end of clone #188. A restriction map of pγ4/1 is shown in FIG. 4.

EXAMPLE 8
Construction of Chimeric Mouse/Human (γ4;κ) anti-CEA H- and L-chain Ig Genes and Insertion of these Genes into Separate Vectors Chimeric constructs holding chimeric mouse/human anti-CEA H- and L-chain genes, respectively, are constructed and are sequentially transferred into host cells with the help of two expression vectors as described in the following (examples 8 and 9).

Unless otherwise stated experimental procedures are those described in Maniatis et al. ("Molecular Cloning: A laboratory manual", Cold Spr. Harbor, N.Y., 1982).

8.1 Molecular Cloning of a Mouse DNA Segment Containing the L-chain Ig Enhancer Element An approximately 475 bp AluI DNA restriction fragment containing the mouse L-chain Ig enhancer of RNA transcription (Picard & Schaffner, Nature 307, 80, 1984; nucleotides 3691–4164 of the Balb/c mouse L-chain Ig locus, EMBL data base sequence entry MUSIGKJC2) is cloned by blunt-end ligation into the pUC12 plasmid vector linearized using the restriction endonuclease SmaI. Ligated DNA is transformed into competent *E. coli* K12/803, and clones are selected after overnight growth on nutrient agar (Oxoid) plates containing 50 μg/ml of ampicillin. Of the two orientations of insert DNA possible a clone is selected containing the plasmid pEL22, the restriction map of which is shown in FIG. 3. pEL22 contains the 475 bp mouse AluI DNA fragment in the same orientation as in the mouse genome, with its 3' end adjacent to the EcoRI site in the pUC12 vector. Its orientation is determined by nucleotide sequencing with the Sanger sequencing protocol described in Example 4.3, using the modifications for direct sequencing of plasmid DNA molecules (Chen & Seeburg, DNA 4, 165, 1985). The sequencing primer used is the Amersham reverse sequencing primer (Cloning and Sequencing Handbook, Amersham International PLC, UK).

8.2 The Chimeric L-chain Gene (pCEA-CκGa)

The scheme for the construction of pCEA-CκGa is shown in FIG. 3. Plasmid pDA14a (Example 7.2) and plasmid pEL22 (Example 8.1) are digested to completion with restriction endonuclease EcoRI. The 2.5 kb EcoRI DNA fragment insert of pDA14a is separated from vector sequences by 1% (w/v) agarose gel electrophoresis and recovered by ethanol precipitation after phenol/CHCl$_3$ extraction (Example 3.2). Equimolar amounts of EcoRI-cut pEL22 and pDA14a 2.5 kb DNA insert are ligated together overnight at 4° C. using T4 DNA ligase (Boehringer) and transformed into competent *E. coli* K12/803. Ampicillin-resistant colonies are selected by plating on nutrient agar plates containing 50 μg/ml of ampicillin and incubating overnight at 37° C. Single colonies are selected and plasmid DNA is prepared from 5 ml mini-cultures according to the procedure described by Ish-Horowicz & Burke (Nucleic Acids Res. 9, 2989, 1981). Digestion of recombinant plasmids using the restriction endonuclease XbaI is used to determine the orientation of the 2.5 kb EcoRI fragment with respect to the transcriptional enhancer-containing element of pEL22. A clone containing these fragments in the desired orientation is selected and plasmid DNA isolated. The corresponding recombinant plasmid is referred to as pKY14a. DNA of pKY14a is partially digested using the restriction endonuclease XbaI, extracted with phenol/CHCl$_3$ and recovered by ethanol precipitation. After recovery, the DNA is treated with Klenow DNA polymerase-I fragment (Boehringer) in the presence of dNTPs to perform a filling-in reaction on the XbaI-cleaved DNA termini. Flush-ended DNA fragments are blunt-end ligated in the presence of T4 DNA ligase (Boehringer), transformed into competent *E. coli* K12/803, and plasmid DNA mini-preparations made from individual ampicillin-resistant clones, as described above. Restriction mapping of recombinant plasmids by terminal digestion using HindIII+XbaI is used to identify a plasmid recombinant (pXba5.5) containing a deleted XbaI restriction site at the position indicated in parentheses in FIG. 3.

The complete DNA insert (approximately 3 kb) of pXba5.5 is isolated by partial digestion of the plasmid with EcoRI followed by complete digestion with SalI, separation from vector DNA sequences by 1% (w/v) agarose gel electrophoresis, followed by phenol/CHCl$_3$ extraction and ethanol precipitation as described above. The approximately 2 kb insert DNA fragment of pCEA-L2a is similarly recovered after terminal digestion with EcoRI/SalI. The recovered DNA fragments are quantified. The eukaryotic plasmid vector pSV2gpt (Mulligen & Berg, Science 209, 1422, 1980) is digested to completion using EcoRI and DNA similarly extracted with phenol/CHCl$_3$, recovered after ethanol precipitation and quantified. Equimolar amounts of EcoRI-cut pSV2gpt, the 2 kb EcoRI/SalI mouse DNA fragment of pCEA-L2a, and the 3 kb SalI/EcoRI mouse DNA fragment of pXba5.5 are ligated together in a three-way ligation reaction in the presence of T4 DNA ligase (Boehringer). Recombinant plasmids are again selected as described above and those with the correct orientation of DNA fragments characterized by restriction mapping. One recombinant designated pCFA-CκGa contains the DNA fragments in the orientation shown in FIG. 3. The selectable marker gene (gpt) derived from pSV2gpt and the resulting chimeric mouse/human L-chain Ig gene have the same transcriptional polarity.

8.3 Molecular Cloning of a Mouse DNA Segment Containing the H-chain Ig Enhancer Element A 1.6 kb HindIII/EcoRI DNA segment from the Balb/c mouse genome (nucleotide positions 1963–3559, EMBL data bank sequence entry MUSIGCDO7) is treated with Klenow DNA polymerase-I fragment (Boehringer) in the presence of dNTPs in order to generate a blunt-ended, double-stranded DNA molecule. The DNA is extracted with phenol/CHCl$_3$ and recovered after ethanol precipitation. Double-stranded HindIII DNA linkers are added by ligation in the presence of T4 DNA ligase (Boehringer) and the extraction/precipitation procedure repeated. The DNA fragment is then treated with restriction endonucleases HindIII+ XbaI, and the smaller of the two XbaI/HindIII fragments generated (approximately 670 bp) is isolated after separation from the other by 1% (w/v) agarose gel electrophoresis. This fragment is cloned in an XbaI/HindIII-cleaved pUC13 μplasmid vector using procedures described in Example 8.2. The resulting plasmid, referred to as pDA4 (FIG. 4), contains the mouse H-chain Ig enhancer of transcription.

8.4 The Chimeric H-chain Gene (pCEA-γ4Na)

The mouse Ig enhancer-containing fragment of pDA4 is recovered after cleavage with EcoRI+HindIII by agarose gel electrophoresis/phenol-CHCl$_3$ extraction/ethanol precipitation. The 3 kb EcoRI/HindIII DNA insert of pγ4/1 is similarly isolated. The two fragments are ligated together with pBR322 plasmid vector DNA linearized by digestion with EcoRI. After transformation into E. coli K12/803, recombinants are selected and plasmid DNA mini-preparations made. Restriction mapping using EcoRI, HindIII and PstI leads to the identification of recombinant clones containing the desired DNA fragments. One of these clones is designated pDA16a (FIG. 4). The approximately 3.7 kb insert DNA fragment of pDA16a is recovered after terminal digestion using restriction endonucleases XbaI and EcoRI, followed by agarose gel electrophoresis/phenol-CHCl$_3$ extraction/ethanol precipitation. The approximately 1.7 kb EcoRI/XbaI fragment of pH8a1, containing the rearranged V-D-J4 H-chain segment of the H8 gene is similarly purified. The two fragments are quantified and ligated together in equimolar amounts in a three-way ligation reaction with pSV2neo (Southern & Berg, J. Mol. App. Genet. 1, 327, 1982) linearized using EcoRI restriction endonuclease in the presence of T4 DNA ligase (Boehringer). After transformation into E. coli K12/803, recombinants are selected as described above and characterized by restriction mapping using the restriction endonucleases EcoRI, HindIII, PstI and XbaI. A recombinant with the desired orientation of DNA fragments is designated pCEA-γ4Na. In this plasmid the selectable marker gene (neo) derived from the vector pSV2neo has the same transcriptional polarity as the mouse/human chimeric H-chain Ig gene.

EXAMPLE 9

Transfection and Expression of Chimeric Mouse/Human Ig Genes pCEA-CκGa and pCEA-γ4Na in Mouse Lymphoid Cells Sp2/0 (ATCC CRL 1581) is a well-characterized mouse cell line of lymphoid origin. It is an Ig non-secreting variant of a cell line obtained from the fusion of a mouse spleen cell with the myeloma X63-Ag8, a subline of the myeloma MOPC-21 (Koehler & Milstein, Eur. J. Immunol. 6, 511, 1976; Shulman et al., Nature 276, 270, 1978). Sp2/0 cells grown in supplemented DMEM as described in Example 2 are harvested by gentle centrifugation (130 g, 4° C.) in 50 ml sterile tubes (Falcon 2070) and washed/resuspended in PBS-CM (Seromed) at a concentration of approximately $1\times10^8$ cells/ml at 4° C. Cells are kept on ice for up to 30 min.

9.1 Transfection of Sp2/0 with the Chimeric H-chain Ig Gene pCEA-γ4Na

Transfection of the chimeric H-chain gene construct (pCEA-γ4Na) is achieved by addition of 20 μg of supercoiled pCEA-γ4Na DNA in 50 μl of TE buffer to $1\times10^7$ Sp2/0 cells in 200 μl of PBS-CM in a sterile plastic tube, on ice. The cells are drawn into the barrel of a TA750 electrotransfection apparatus (Kruess GmbH, Hamburg, W. Germany) and subjected to one electrical pulse of 3500 V/cm for 10 μs, using the cylindrical electroporation chamber provided by the manufacturers, pre-cooled by drawing sterile, ice-cold PBS-CM into the barrel of the apparatus before use. Cells are expelled gently into a clean, sterile cryotube (Nunc) and kept on ice for 10 min, after which they are incubated at room temperature for a further 20 min after dilution (1:3; v/v) with growth medium (see above). Cells are then distributed into 96 wells in two 48-well tissue culture clusters (Costar) at a cell density of approximately $1\times10^5$ cells/well in 1 ml of DMEM growth medium containing 15% FCS, 1 mM sodium pyruvate, 10 mM Hepes, 1 mM glutamine, 100 μM gentamycin (Gibco), 5 ng/ml insulin+5 ng/ml transferrin+5 μg/ml selenium (CR-ITS premix., Collaborative Res. Inc.), 56 μg/ml folic acid (Seromed), 36 μg/ml L-asparagine (Calbiochem), 116 μg/ml L-arginine HCl (Calbiochem). After incubation for 48 h at 37° C. in a humidified atmosphere containing 7.5% CO$_2$ (Heraeus Cytoperm incubator), transfected cells are selected by addition of 1 mg/ml of G418-sulphate (Geneticin, Gibco 066-1811). Medium and drug are changed every 2 days. Cells are screened for the expression of human IgG after 14 days using the "dot" assay described in Example 9.2.

9.2 Selection of Transfectants Containing Intracellular Human Ig H-chain Polypeptide No H-chain Ig protein is expected to be detected in the medium of Sp2/0 cells transfected with the chimeric H-chain gene construct alone, because H-chains are only secreted after they become associated with L-chains, but Sp2/0 cells do not contain functional L-chain polypeptide. Confirmation of expression of intracellular H-chain polypeptides in cells transfected with the chimeric Ig H-chain gene pCEA-γ4Na is performed as follows. Transfected cells ($1\times10^5$) are collected from culture medium by gentle centrifugation, washed with PBS and resuspended in 10 μl of H$_2$O. Cells are ruptured by three rounds of freezing in dry ice and thawing at 37° C. Cell debris is removed by centrifugation at 5'000 g (Eppendorf Microcentrifuge) at room temperature. The intracellular heavy chain expression is analysed by a procedure described by Towbin & Gordon (J. Immun. Meth. 72, 313, 1984) by dotting samples (1 μl) of the supernatant on to acetate cellulose membrane (Millipore HAWAG, 0.45 μm pore size). After blocking non-specific binding by incubating membranes in RIA-buffer (1% BSA (Fluka Fraction V, 05480), 0.2% NaN$_3$ (Merck), 0.1% phenol red (Seromed) in PBS) at 37° C. for 20 min, they are washed in PBS and then incubated for 2 h at 37° C. in developing serum containing goat-anti-human IgG (alkaline phosphatase-labelled, Tago) at a dilution of 1:1000 in RIA-buffer. Membranes are washed 6× in PBS followed by 6× in H$_2$O, after which they are incubated at room temperature for 15 min in substrate buffer consisting of a 1:1 mixture of the following two solutions prepared immediately before use: (a) 1 mg/ml of Fast Blue B salt (Fluka, 44660) in H$_2$O; (b) 1 mg/ml of 2-naphthylphosphate, monosodium salt (Fluka, 71100) in 60 mM borate buffer, pH 9.7. The reaction is stopped by incubating membranes in methanol:acetic acid:water (5:1:5, v/v). Viable cells, corresponding to those giving strong color signal signifying alkaline phosphatase activity (thus expressing high levels of intracellular human IgG heavy chain), are cloned. From several such cloned cell lines, one (EFVIII/γ4Na75-75) is chosen for a second round of transfection with the chimeric L-chain gene construct plasmid pCEA-CκGa.

9.3 Transfection of EFVIII/γ4Na75-75 with the Chimeric L-chain Ig Gene pCEA-CκGa Cells of EFVIII/γ4Na75-75 or any other cell line prepared according to Example 9.2 are expanded by growth in the medium described in Example 2. Approximately 1×10$^7$ cells are collected by gentle centrifugation, and washed/resuspended in 200 μl of PBS-CM on ice. Cells are then transfected using 10 μg of supercoiled pCEA-CκGa DNA, and transfectants plated in tissue culture clusters using the procedure described in Example 9.2. After growth for 60 h transfected cells are selected using growth medium containing 0.125 μg/ml of mycophenolic acid (Calbiochem, 475913, from Behring Diagnostics), 250 μg/ml of xanthine, and a 1:45 dilution of hypoxanthine/thymidine (HT, 50× conc., Boehringer, 623091). The concentration of mycophenolic acid is increased to 0.5 μg/ml within the following 14 day growth period, keeping the amount of HT and xanthine constant. After this period, cell culture medium from wells of tissue culture clusters is assayed for secreted human IgG, as described in Example 9.4.

9.4 Antibody Detection Assay and Determination of Level of Secreted Human IgG in Transfected Cells Flat-bottomed micro-ELISA plates (Immulon, Dynatech, M129A) are coated either with 1 μg/well of goat-anti-human κ antibody (Tago, 060401) or with 500 ng/well of purified human carcinoembryonic antigen (Tu241, a gift from Prof. J.-P. Mach, Department of Biochemistry, University of Lausanne), by incubation overnight at 4° C. After washing with PBS, non-specific binding is blocked by incubating with RIA-buffer (Example 9.2) for 20 min at 37° C. in a humidified chamber, followed by further washing with PBS. Cell supernatants (50 μl) are added and incubated for 2 h at 37° C. After washing with PBS, bound chimeric antibody is developed using alkaline phosphatase-labelled goat-anti-human IgG antibody (Tago, 902002) at the recommended dilution (1:1000) in RIA-buffer. Plates are incubated for 2 h at 37° C. Plates are washed several times with PBS before addition of 150 μl of substrate buffer which consists of 2 tablets of phosphatase substrate (p-nitrophenylphosphate, Sigma, 104R) in 10 ml of substrate buffer (800 ml of H$_2$O, 97 ml of diethanolamine, 130 ml of 1 M HCl, 200 mg of NaN$_3$, 200 mg of MgCl$_2$·6H$_2$O, pH adjusted to 9.7. After incubation for 15 min at 37° C. the color reaction is stopped by addition of 50 μl of 1 M NaOH. $E_{405-495}$ is measured using a Titertek Multiscan MC. Viable cells from parallel wells having high levels of secreted human IgG are cloned. One of several such clones is designated EFVIII/γ4Na75-75/CκGa5-6 (referred to as CE 75-5-6) and was deposited at the "Collection Nationale de Cultures de Microorganismes" of the Institut Pasteur, Paris, on Dec. 15, 1987, under the number I-720.

For quantitation of the amount of chimeric antibody (γ4;κ) secreted by CE 75-5-6, several standard human IgG4κ myeloma proteins (from Dr. F. Skvaril, Institute of Cancer Research, Berne) are used. Based on this test the transfectoma CE 75-5-6 secretes 1 μg/ml of chimeric antibody into the culture medium after 6 days growth.

EXAMPLE 10

Construction of Chimeric Mouse/Human (γ4;κ) Anti-CEA H- and L-chain Genes and Insertion of these Genes into a Double-construct Vector Chimeric constructs containing chimeric mouse/human anti-CEA H- and L-chain-genes, respectively, are constructed and are transferred into host cells with the help of a single vector comprising chimeric H- as well as L-chain genes as described in the following examples 10 and 11.

Unless otherwise stated experimental procedures are those described in Maniatis et al. ("Molecular Cloning: A laboratory manual", Cold Spr. Harbor, N.Y., 1982).

10.1 Molecular Cloning of a Mouse DNA Segment Containing the L-chain Ig Enhancer Element (Mouse Ig L-chain-ΔCκ r Precursor)

The mouse Cκ gene is deleted from the germline sequences by isolating a 2 kb PstI/XmnI and a 1.1 kb XmnI/BamHI fragment from pLCEA/14A. (Walfield et al., Nucl. Acids Res. 8, 4689, 1980). This plasmid contains the mouse NS2 Cκ light chain gene, rearranged at the J2 joining segment, on a 7.0 kb BamHI/BamHI restriction fragment. This fragment is equivalent to the 7.0 kb BamHI/BamHI fragment derived from MOPC21/NS-1n as described by Walfield et al. (see above). The exact sequence of the 3.9 kb PstI/BamHI fragment is given in the EMBL data base entry MUSIGKJC2, nucleotide positions 2368–6258.

Figure 5:
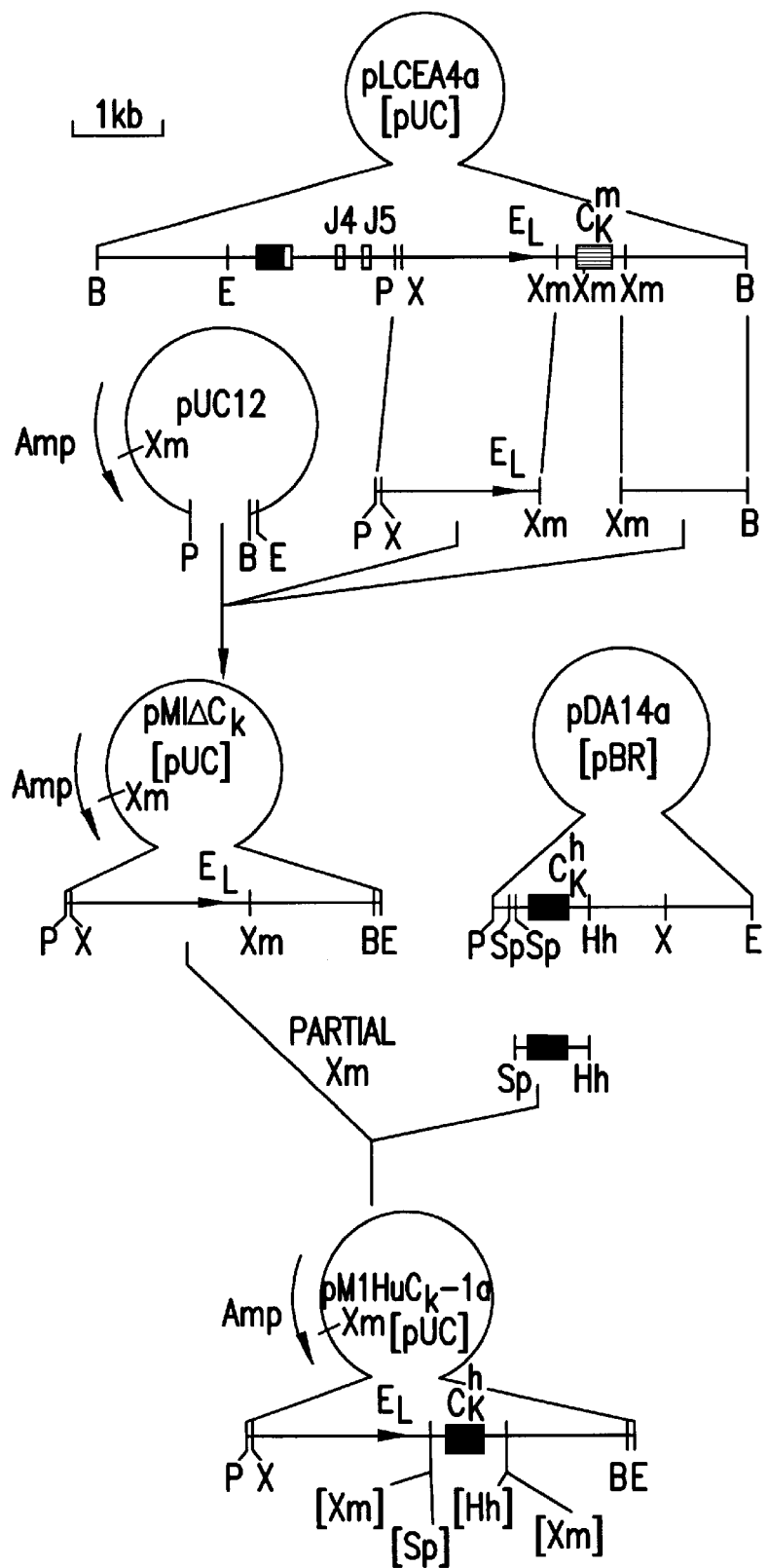

The cloning of these two fragments into the vector pUC12, double-restricted with PstI and BamHI, creates a recombinant plasmid designated pM1ΔCκ. The resultant cloned fragment contains germline sequences from the mouse immunoglobulin light chain locus starting at the PstI site, 268 bp downstream of the J5 joining segment, through to the BamHI site, 3884 bp downstream of the PstI site. Nucleotide positions below are indicated relative to the first base of this PstI recognition seqeunce. The fragment includes the mouse Ig Cκ enhancer sequences at 1542–1666 in its original germline configuration. The mouse Cκ coding region has been deleted between positions 2021 and 2754 using existing XmnI sites at these positions, recreating an XmnI site at the junction of the deleted Cκ gene. The total PstI/BamHI fragment measures 3152 bp and now has a unique XmnI site at the site of the deleted mouse Cκ gene at position 2017-2026, for cloning purposes. A restriction map of pM1ΔCκ is shown in FIG. 5.

10.2 The chimeric L-chain gene (pMceaCκ$^h$-1a)

The human Cκ coding sequences are isolated from plasmid pDA14a, a pBR322 recombinant, containing a 2.5 kb EcoRI/EcoRI fragment within which is located the ca. 320 bp human Cκ coding region. This plasmid has been described in Example 7.2 and a restriction map is shown in FIGS. 3 and 5. A 724 bp SphI/HhaI fragment is purified and the 3' protruding ends trimmed with bacteriophage T4 DNA-polymerase. The fragment starts 106 bp 5' and extends 296 bp 3' of the human Cκ coding region. It includes also the polyadenylation site which lies 177 bp 3' of the Cκ coding sequence.

pM1ΔCκ contains two XmnI sites, one at the junction of the deleted mouse Cκ sequences and one in the β-lactamase coding sequence derived from pUC12, which confers resistance to ampicillin. pM1ΔC is partially restricted to ampicillin. pM1ΔCκ is partially restricted with XmnI and the linear form gel-purified. 50% of this material is restricted at the XmnI site in the β-lactamase coding sequence, 50% is restricted at the required former mouse Cκ location.

Insertion of the human Cκ fragment in the first XmnI site results in a recombinant plasmid without a functional β-lactamase gene, hence only recombin ant s are found which contain the human Cκ fragment at the position of the former mouse Cκ region. Two orientations are possible. The recombinant plasmid containing the human Cκ fragment in the correct orientation, N-terminus closest to the mouse enhancer region, is identified by restriction analysis of the recombinant plasmids with restriction endonuclease AvaII. This plasmid is designated pM1HuCκ-1a.

Figure 6:
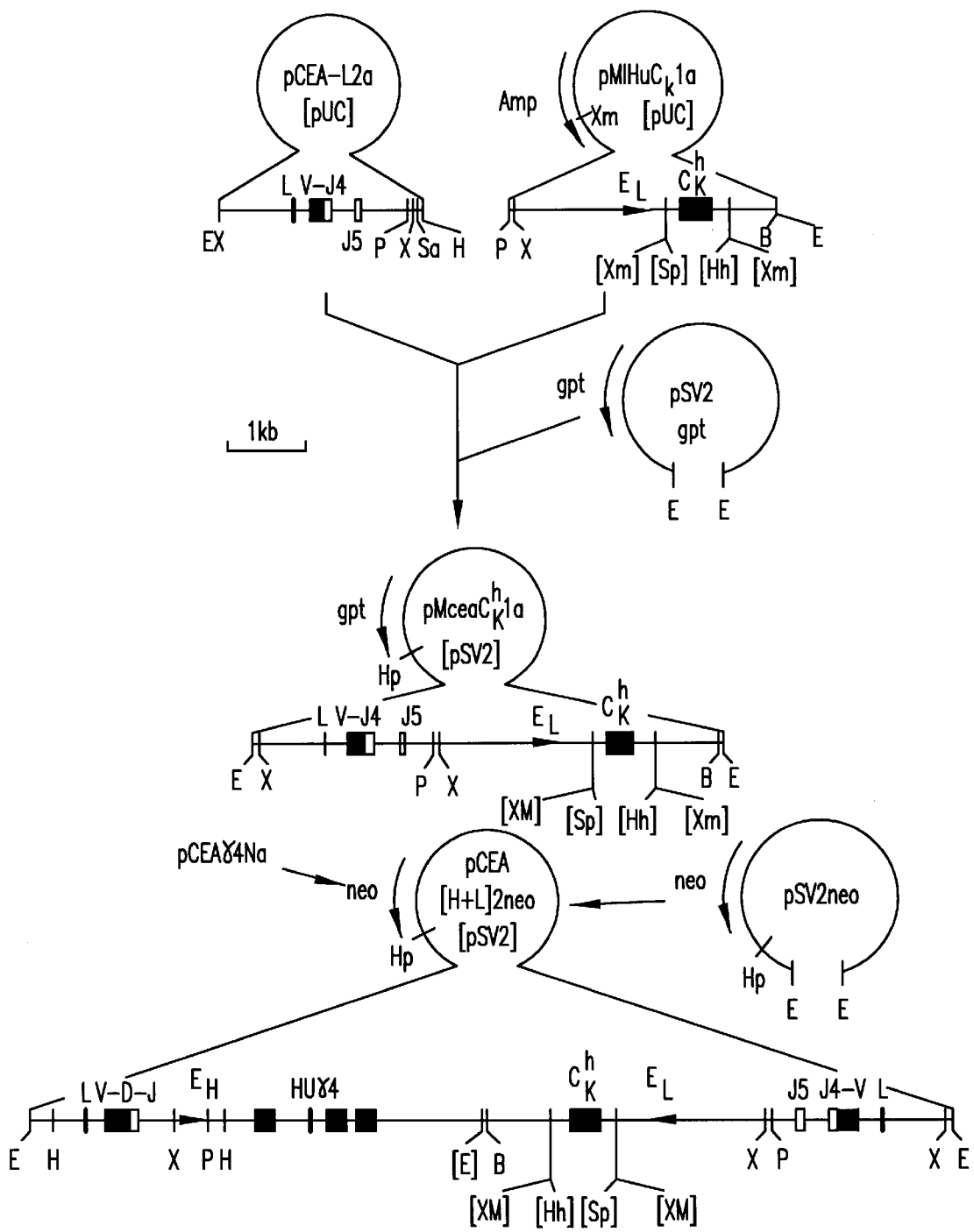

The mouse CEA light chain sequences are isolated from the recombinant plasmid pCEA-L2a. This plasmid contains an 1.9 kb XbaI/XbaI fragment coding for the functional variable part of the mouse anti-CEA light chain and is described previously (Example 4.2). A restriction map is shown in FIGS. 1A, 3 and 6.

By partial XbaI restriction followed by total EcoRI restriction, the mouse anti-CEA light chain variable segment is isolated on a 1.9 kb EcoRI/XbaI fragment. This fragment has an extra 24 bp derived from the pUC12 polylinker, including restriction sites for BamHI, SmaI and SacI. These sites lie 5' of the mouse variable anti-CEA coding region. In the final genomic construct they are positioned at the junction of the recombinant fragment and the expression vector.

The 1.9 kb EcoRI/XbaI fragment is joined to the 3.8 kb PstI/BamHI fragment from pM1HuCκ-1a described above, containing the mouse Ig Cκ enhancer and the human Cκ coding region. For cloning purposes it is isolated as an XbaI/EcoRI fragment using the XbaI site 18 bp downstream of the PstI site and the EcoRI site in the pUC12 polylinker, which adds 18 bp downstream of the BamHI site including SmaI and SacI restriction sites. These polylinker sequences are positioned at the second junction of recombinant fragment and expression vector.

The two fragments are joined and cloned into the expression vector pSV2gpt, restricted with EcoRI, in a three way ligation. Two orientations of the fragment, relative to the gpt gene, are isolated, either both gpt and mouse variable anti-CEA-human Cκ in the same transcriptional orientation (orientation a) or in opposite transcriptional orientation (orientation b). Both orientations are identified by double restriction with restriction endonucleases HindIII and PstI. They are designated pMceaCκ$^h$-1a and pMceaCκ$^h$-1b. Their DNA insert contains the full coding region of the mouse variable anti-CEA-human Cκ constant immunoglobulin light chain in the original mouse genomic configuration. The fragment is recovered as a single EcoRI/EcoRI fragment of ca. 5.7 kb.

10.3 The Chimeric H-chain Gene (pCEA-γ4Na)

The chimeric H-chain gene pCEA-γ4Na is constructed as described in examples 8.3 and 8.4.

10.4 The Chimeric Double-construct Holding Both Mouse/Human (γ4;κ) Anti-CEA H- and L-chain Ig Genes (pCEA(H+L)2neo)

Both the mouse anti-CEA-human constant chimeric light and heavy chain are contained on a single EcoRI/EcoRI fragment, the light chain on a 5.7 kb fragment in pMceaCκ$^h$-1a, the heavy chain on a 5.3 kb EcoRI/EcoRI fragment in pCEA-γ4Na.

By joining the light and heavy chain EcoRI/EcoRI fragments and destroying the EcoRI site at the junction, a double gene construct is created where all coding sequences and regulatory sequences for the mouse/human (γ4;κ) anti-CEA H- and L-chain Ig genes are located on an 11,0 kb EcoRI/EcoRI fragment.

pMceaCκ$^h$-1a and pCEA-γ4Na are partially restricted with EcoRI followed by filling in of the 5' overhang with the large fragment of E. coli DNA polymerase I (Klenow fragment). The linear form of each plasmid is gel purified followed by double restriction with restriction endonucleases EcoRI and HpaI. This releases the chimeric fragment from the pSV2gpt or pSV2neo vector, respectively, since the only restriction sites for HpaI are in the two vectors. Only one of the EcoRI 5' ends of each fragment is a blunt end. The other end remains a 'sticky' 5'-EcoRI overhang. The two fragments are ligated together in a 1:1 ratio with bacteriophage T4 ligase to form concatemeric molecules. A certain number of the light chain fragments are joined to a blunt-end of a heavy chain fragment. Total restriction with EcoRI produces a certain number of 11.0 kb EcoRI/EcoRI fragments of which a third part is a light chain joined to a heavy chain mouse/human (γ4;κ) anti-CEA chimeric fragment. The remaining two thirds consist of heavy-heavy and light-light chain dimers which are presumably not clonable.

Gel purification of the ca. 11.0 kb EcoRI/EcoRI fragments followed by cloning into the pSV2neo or pSV2gpt expression vector, restricted with EcoRI, and transformation to competent E. coli K12/803 results in a number of recombinant plasmids. These are screened by colony hybridization to the 1.9 kb XbaI/XbaI fragment coding for the mouse anti-CEA variable light chain sequences, isolated from plasmid pCEA-L2a (Example 4.2). DNA is prepared from positive colonies and recombinant plasmids having both the heavy and light chain mouse/human (γ4;κ) anti-CEA chimeric DNA fragments are identified by restriction enzyme analysis with restriction endonucleases EcoRI, XmnI and PstI. One recombinant plasmid obtained this way is designated pCEA(H+L)2neo. The anti-CEA light and heavy chain chimeric fragments are arranged in opposite transcriptional orientation. The anti-CEA heavy chain fragment is in the same transcriptional orientation as the neo gene in pSV2neo. The EcoRI site at the junction of the anti-CEA light and heavy chain chimeric fragments is destroyed but the expected XmnI site, which is created by joining two blunted EcoRI sites, is not present. From this double chimeric gene construct the mouse/human (γ4;κ) anti-CEA light and heavy chain coding and regulatory sequences are isolated as a single ca. 11.0 kb EcoRI/EcoRI fragment. A restriction map of pCEA(H+L)2neo is shown in FIG. 6.

EXAMPLE 11

Transfection and Expression of the Chimeric Mouse/Human (γ4;κ) Anti-CEA Ig H- and L-chain Double Gene Construct pCEA(H+L)2neo in Mouse Lymphoid Cells Transfection of the chimeric mouse/human (γ4;κ) anti-CEA Ig gene double-construct pCEA(H+L)2neo is achieved by isolation of the coding regions of the mouse/human (γ4;κ) anti-CEA H- and L-chains on a single ca. 11.0 kb EcoRI/EcoRI DNA fragment from pCEA(H+L)2neo. 15 μg of this fragment are mixed with 1,5 μg pSV2neo, linearized with EcoRI, in 50 μl of TE buffer and subsequently transfected to Sp2/0 mouse lymphoid cells, exactly as described in example 9 for the chimeric mouse/human (γ4;κ) anti-CEA single Ig gene constructs.

Selection for neomycin resistance, antibody detection and determination of level of secreted IgG in transfected cells are carried out exactly as described in Example 9.2 and 9.3, respectively. One clonal cell line isolated in this manner and selected for high expression of the chimeric monoclonal antibody is designated EFIX-pCEA-Ig-(γ4;Cκ) 4-8-13 (referred to as CE 4-8-13) and was deposited at the "Collection Nationale de Cultures de Microorganismes" of the Institut Pasteur, Paris, on Nov. 22, 1988, under the number I-818.

The transfectoma CE 4-8-13 secretes 10 µg/ml of chimeric antibody into the culture medium after 6 days growth, as determined by the procedures described in example 9.4.

EXAMPLE 12

Characterization of the Chimeric Monoclonal Antibody

Figure 7:
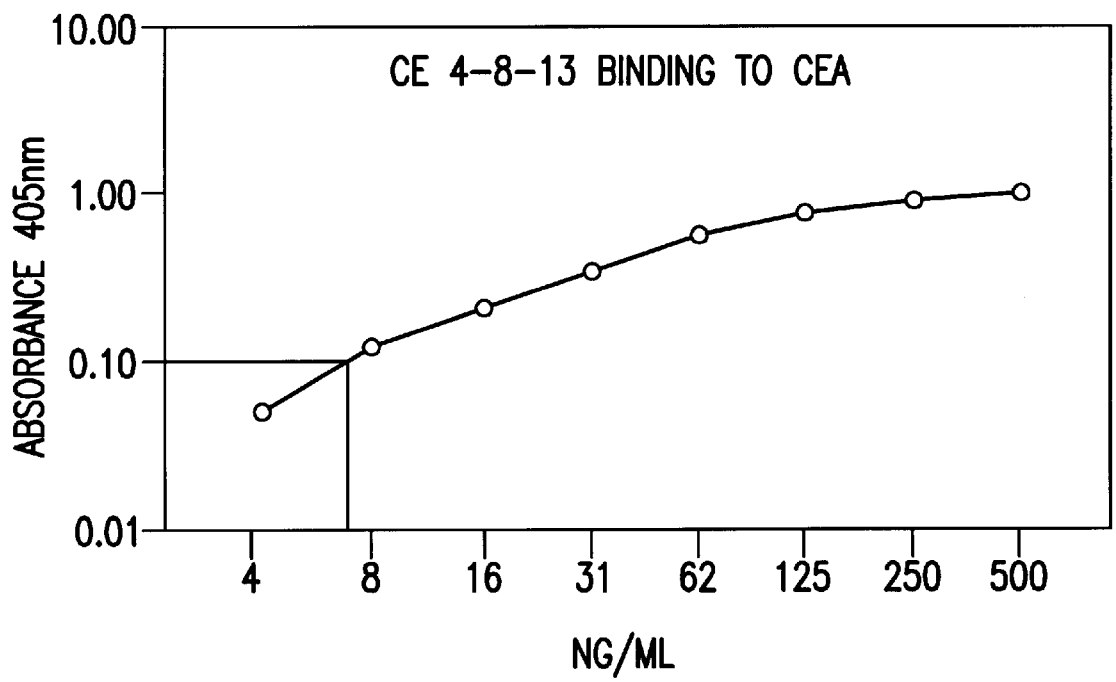

The binding of the chimeric monoclonal antibody (γ4;κ) to CEA is determined by the ELISA test described in Example 9.4 for the selection of chimeric antibodies. With the chimeric anti-CEA MAb secreted by the cell line CE 4-8-13, less than 8 ng/ml of the MAb is required to result in an optical density of 0.1 in the test (see FIG. 7). For competition tests, purified CEA antigen and a purified Ig fraction from mouse ascites fluid generated from the CE 25 hybridoma are used. Methods used are based on published procedures (Voller et al., "Manual of Clinical Immunology", 1976, 506). The binding of the chimeric antibody to purified CEA in the ELISA test is inhibited either by soluble CEA or with purified murine CE 25 antibody. Over 99% of secreted chimeric monoclonal antibody can be absorbed on immobilized CEA antigen. Whereas the parental CE 25 hybridoma produces a murine (γ1;κ) antibody when developed using goat-anti-mouse $IgG_1$ (alkaline phosphatase labelled), CE 75-5-6 and CE 4-8-13 do not.

The above immunological tests demonstrate that the antibody secreted by cell lines CE 75-5-6 and CE 4-8-13:

(a) bind to the CEA antigen;

(b) possess human constant region (γ4;κ) determinants and lack corresponding determinants of mouse origin;

(c) are inhibited by the corresponding murine antibody produced by hybridoma CE 25;

(d) bind specifically to the CEA antigen, since their binding is inhibited by soluble CEA;

(e) are produced at high levels in transfectomas containing the chimeric H- and L-chain Ig genes as described above (1 µg/ml by CE 75-5-6; 10 µg/ml by CE 4-8-13).

EXAMPLE 13

Isolation and Purification of Chimeric Monoclonal Antibodies for Diagnostic/Therapeutic Purposes 13.1 In Vitro Synthesis A cell line as described above synthesizing the chimeric monoclonal antibodies is grown on the glass beads of a packed bed column.

The preculture for this column is prepared as follows: The cells from 4 confluent 175 cm² tissue culture flasks are used to inoculate one Nunc stapler. The adherent cells are detached from the flask by rinsing the confluent cell layer with a trypsin/Versene solution made up of equal volumes of trypsin solution (Gibco, 0.5 g/l) and Versene (Gibco, 1:5000). 4×10⁶ cells are suspended in 400 ml of modified conditioned DMEM medium ($DMEM_{med}$=DMEM containing in addition 1 mM Na-pyruvate, 2 mM glutamine, 50 µM 2-mercaptoethanol, 10 mM Hepes and, if not indicated otherwise, 10% FCS). The volume of the suspension is brought to 500 ml by adding fresh $DMEM_{med}$. 500 ml cell suspension are transferred to a Nunc stapler and incubated at 37° C. in an atmosphere of air containing 10% $CO_2$. Four, seven and ten days after inoculation, additional medium (3×500 ml) is added. Fourteen days after inoculation the cells are harvested and used to inoculate the packed bed reactor. The conditioned medium is first removed from the stapler. 500 ml trypsin/Versene solution is added to the stapler and the entire cell layer is soaked with this solution. Free trypsin/Versene solution is poured off and the cell layer is left in contact with remaining trypsin/Versene for 5 min. 500 ml conditioned medium is added back to the cells. The cells are detached by shaking the stapler thoroughly. An additional 1.5 L of conditioned medium are added to the stapler and the entire suspension is then transferred to the packed bed reactor. The reactor consists of a 10 l cylindrical glass vessel filled with boro-silicate glass beads of 2 mm diameter. The medium is circulated through the reactor by an external pump at a rate of 45 l/h. The dissolved oxygen concentration and the pH of the circulating medium is measured and controlled continuously. Pure oxygen is used to keep the minimal dissolved oxygen level above 10% saturation and $CO_2$ and 1.0 NaOH are used to control the pH between 7.0 and 7.3. The liquid volume in the reactor and the external circuit is 5 l. The system is kept in a water bath at 37° C. After inoculation the cells are allowed to grow in a $DMEM_{med}$ medium containing 10% serum. As soon as the glucose level in the medium drops below 1 g/l continuous exchange of medium is initiated at a rate of 2 l/ day. When the level of dissolved oxygen decreases to 20% the serum concentration in the feed medium is lowered to 1.25%. Two days later the exchange ratio is increased by 1 l/ day. On subsequent days the exchange rate is increased further until a maximum value of 5 L/ day is reached. From this time onward the outflowing medium is collected for the isolation and purification of the chimeric antibody.

13.2 Isolation and Purification of Chimeric Monoclonal Antibodies

The culture medium is filtered using a Minitan ultrafiltration system (Millipore Corp., Bedford, Mass.), through a 0.1 µm cassette filter (type VVLPOMPO4, Millipore). The filtrate is concentrated 10-fold using the Minitan ultrafiltration system fitted with 30,000 MW cut-off filter cassettes (type PTTKOMPO4, Millipore). The concentrated retentate is then prepared for chromatography on protein-A Sepharose by addition of glycine and NaCl to a final concentration of 1.5 M glycine and 3 M NaCl and the pH adjusted to 8.6 with 5 M NaOH. After passing the culture medium concentrate through a column containing protein-A Sepharose CL-4B (Pharmacia, Uppsala, Sweden), unbound material is washed from the column with binding buffer (1.5 M glycine, 3 M NaCl, pH 8.9 with NaOH) and the column eluted with a stepwise gradient of decreasing pH consisting of 100 mM citric acid adjusted to pH 3.0, 4.0, 5.0 and 6.0 with 5 M NaOH as described in the Pharmacia application note (Separation News Vol. 13, No. 5). The highest concentration of chimeric antibody is determined by an ELISA test to elute at pH 4.0.

EXAMPLE 14

Determination of CEA with an Enzyme-linked Immunosorbent Assay (ELISA)

14.1 Labelling of Chimeric Monoclonal Antibodies with Alkaline Phosphatase 1.4 mg of a chimeric monoclonal antibody in 1.4 ml of PBS are coupled for 2 h with a solution containing 5 mg of alkaline phosphatase (Sigma P6774, type VII-T) according to the standard method of Voller et al. (Bull. World Health Organ. 53, 55, 1976) using glutaraldehyde (0.2% v/v). The conjugate is transferred into 5 ml of Tris buffer 0.05 M, pH 8.0, containing 1 mM $MgCl_2$, 1% BSA and 0.02% $NaN_3$. The solution is kept in the dark at 4° C.

14.2 Assay Procedure

Polypropylene microtitre plates (Dynatech) are coated over a period of 2 h at 37° C. and overnight at 4° C. with 150 μl of a solution of the . chimeric monoclonal antibody secreted by cell line CE 75-5-6 or CE 4-8-13 (10 μg/ml) in a buffer pH 8.6 (carbonate-buffered 0.9% saline containing 0.02% sodium azide). The plates are washed five times with PBS, and protein-reactive sites still present are saturated by incubation for 1 h at 37° C. with 250 μl of a buffer pH 7.4 (0.2% gelatine and 0.2% NaN$_3$ in PBS). Plates coated in this manner can be kept at 4° C. in this buffer for a few days.

50 μl of a dilution series of a test solution or a standard solution containing purified human CEA, 50 μl of buffer pH 7.4 and 50 μl of a solution of the phosphatase-labelled monoclonal anti-CEA antibody MAb 35 (Haskell et al., Cancer Res. 43, 3857, 1983) recognizing a different CEA-epitope than the chimeric antibody (Example 14.1) diluted 1:100 with buffer pH 7.4 are mixed and incubated in the wells of the microtiter plates for 2 h at 37° C. and for 30 minutes at 4° C. The plates are washed five times with PBS, then incubated for 30 min at 37° C. with 150 μl of a solution of p-nitrophenyl phosphate (1 mg/ml in 10% diethanolamine buffer, 0.5 mM MgCl$_2$, pH 9.8). By measuring the optical density at 405 nm, the amount of released p-nitrophenol is determined, which is proportional to the amount of the bound enzyme phosphatase and hence proportional to the amount of human CEA in the test solution.

The test can also be carried out by using the enzyme-labelled chimeric monoclonal antibody secreted by cell line CE 75-5-6 or CE 4-8-13 and coating the microtitre plates with the monoclonal anti-CEA antibody MAb -35 recognizing a different CEA-epitope than the chimeric antibody.

14.3 Test Kit for ELISA

A test kit for the assay described in Example 14.2 contains:

polypropylene microtiter plates,

- 20 ml of the chimeric monoclonal anti-CEA antibody secreted by cell line CE 75-5-6 or CE 4-8-13 (10 μg/ml) in carbonate-buffered saline (0.9% NaCl, 0.42% NaHCO3, 0.0072% Na$_2$CO$_3$, 0.02% NaN$_3$),
- 1 ml of the alkaline phosphatase-coupled monoclonal anti-CEA antibody MAb 35 recognizing a different CEA-epitope than the chimeric antibody (0.3 mg antibody per ml) in Tris-buffer (0.05 M, 1 mM MgCl$_2$, 1% BSA, 0.02% NaN$_3$, pH 8.0),
- 2 ml of standard solution containing 5 μg purified human CEA,
- 300 ml of PBS,
- 300 ml of buffer pH 7.4 (0.2% gelatine and 0.2% NaN$_3$ in PBS)
- 50 ml of p-nitrophenyl phosphate (1 mg/ml) in diethanolamine buffer (10%, 0.5 mM MgCl$_2$, 0.02% NaN$_3$, adjusted to pH 8.9 with HCl),
- calibration curve,
- color intensity scale,
- instruction manual.

EXAMPLE 15

Pharmaceutical Preparation for Parenteral Application 120 mg chimeric monoclonal antibody prepared according to Example 13 are dissolved in 5 ml physiological saline. The solution is passed through a bacteriological filter, and the filtrate filled in an ampoule under aseptic conditions. The ampoule is preferentially stored in the cold, e.g. at −20° C.

We claim:

1. A recombinant DNA molecule, comprising an insert selected from the group consisting of:

an insert coding for a light chain murine variable region of chimeric monoclonal antibodies or fragments of said antibodies, capable of binding to an epitope of human corcinoembryonic antigen (CEA) not present on non-specific cross reacting NCA$_{55}$ and NCA$_{95}$, on biliary glycoprotein, or on granulocytes, wherein said light chain murine variable region codes for a polypeptide of the formula I

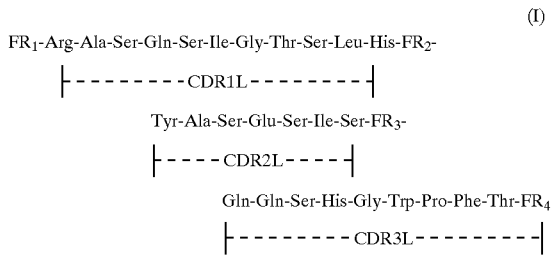

(I)

wherein FR$_1$ is a polypeptide residue having 23–28 naturally occurring amino acids, FR$_2$ is a polypeptide residue having 14–16 naturally occurring amino acids, FR$_3$ is a polypeptide having 14–16 naturally occurring amino acids and FR$_4$ is a polypeptide residue having 9–11 naturally occurring amino acids;

an insert coding for a heavy chain murine variable region of chimeric monoclonal antibodies or fragments of said antibodies, capable of binding to an epitope of human corcinoembryonic antigen (CEA) not present on non-specific cross reacting NCA$_{55}$ and NCA$_{95}$, on biliary glycoprotein, or on granulocytes, wherein said heavy chain murine variable region codes for a polypeptide of the formula II

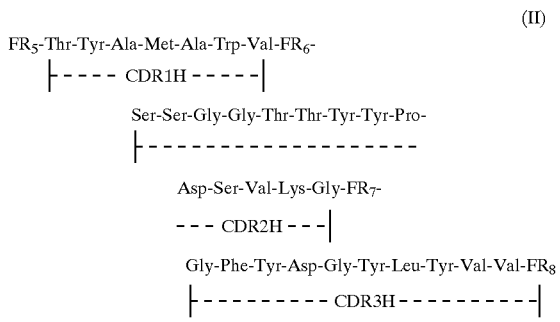

(II)

wherein FR$_5$ is a polypeptide residue having 32–36 naturally occurring amino acids, FR$_6$ is a polypeptide residue having 14–16 naturally occurring amino acids, FR$_7$ is a polypeptide having 32–34 naturally occurring amino acids and FR$_8$ is a polypeptide residue having 12–14 naturally occurring amino acids; and an insert coding for said light chain variable region and said heavy chain murine variable region.

2. A recombinant DNA according to claim 1 comprising an insert coding for a light chain murine variable region specific for human CEA which originates from genomic DNA of the cell line CE 25.

3. A recombinant DNA according to claim 1 comprising an insert coding for the polypeptide of formula I wherein FR$_1$, FR$_2$, FR$_3$ and FR$_4$ are polypeptides of formula IA, IB, IC and ID, respectively.

4. A recombinant DNA according to claim 1 comprising an insert of the formula

```
                                                                    (III)
     TCTAGACTGCTGTGGTCTTTTAAGTAGCATGAAAAACATCTGCTAAAGAAGGAATTAGTT
  1  ---------+---------+---------+---------+---------+---------+   60

TGAACATGCTAGAAATACATCTGTGATACTCTCATCACTCTTGTTGGAAAGATATGCAAG
 61  ---------+---------+---------+---------+---------+---------+  120

AAGCACTATTTGGCTATTATTTGGAAAGTGCTATAATGTATTTTGATATCTCAACCTCTG
121  ---------+---------+---------+---------+---------+---------+  180

AAATTCTTCTGTATGTTGGCAGATTGTAAACCTTTACAAGGCTTTCATTCTCTTCTCTGG
181  ---------+---------+---------+---------+---------+---------+  240

AGAAAAATGTCTTTGTAGGCAATCCAGAATTTCTTATTTCTTGCTAATGAAATCTCCTCA
241  ---------+---------+---------+---------+---------+---------+  200

GTGTGATATCACTTTAGTTTCATGTGTTGTTATGCTTCATGTAATGTTAAGAAAGTTAAA
301  ---------+---------+---------+---------+---------+---------+  360

GATGCTCCAATCCATATTGTAAGAAACATTCCAAGCCATGGAATAAGGCATGGATTTGAG
361  ---------+---------+---------+---------+---------+---------+  420

ATGCTCTTTATTTCAAACTACTGAATATATCTTAGAGATTTCTTTAGACTGTGTTAAATA
421  ---------+---------+---------+---------+---------+---------+  480

TGTAACCATTTAAGTAGGAGTCAAGTCTCCTTTAAATCTCAACAGCTCTTCAGGTAACCA
481  ---------+---------+---------+---------+---------+---------+  540

ACAAAAGGATAAATATTCTAATAAGTCACTAGGAGCATGCTCTTCTGACCAGGTCTTTCT
541  ---------+---------+---------+---------+---------+---------+  600

TATAAGCAACATGAAGACAGTATGATTTGCATAAGTTTTTCTTTCTTCTAATGTCCCTGC
601  ---------+---------+---------+---------+---------+---------+  660

CTCTTAGAGTATTATAAGAAGATCTTTCTAGGGATGTGTCATGGTCCACACAAAAATAGG
661  ---------+---------+---------+---------+---------+---------+  720

M   V   S   T   P   Q   F   L   V   F   L   L   F   W   I   P
                 MetValSerThrProGlnPheLeuValPheLeuLeuPheTrpIlePro
     GAAAGTGTGAAGATGGTATCCACACCTCAGTTCCTTGTATTTTTGCTTTTCTGGATTCCA
721  ---------+---------+---------+---------+---------+---------+  780

GGTAATGACTGTTTGGGTGTGGCAAAAAAGTGGAGATGTTATTTAAATACAAAATTTTCT
781  ---------+---------+---------+---------+---------+---------+  740

TGCTTTATTTGGAAGCCAATGTCACATGGGAATTGACTTTCAGTTTAAAGAAATTGATAC
841  ---------+---------+---------+---------+---------+---------+  900

AATAAAAGTCATTTATTTTTCTAAGTTGTTTAGAAGTGACTTTCATATTCAGTGTTATGA
901  ---------+---------+---------+---------+---------+---------+  960

A   S   R   G   D   I   L   L   T   Q   S
                            AlaSerArgGlyAspIleLeuLeuThrGlnSer
     TCGACTAATGTATCTTCCATTTTTCCAGCCTCCAGAGGTGACATCTTGCTGACTCAGTCT
961  ---------+---------+---------+---------+---------+---------+ 1020

P   A   I   L   S   V   S   P   G   E   R   V   T   F   S   C   R   A   S   Q
     ProAlaIleLeuSerValSerProGlyGluArgValThrPheSerCysArgAlaSerGln
     CCAGCCATCCTGTCTGTGAGTCCAGGAGAAAGAGTCACTTTCTCCTGCAGGGCCAGTCAG
1021 ---------+---------+---------+---------+---------+---------+ 1080

S   I   G   T   S   L   H   W   Y   Q   Q   R   T   N   G   S   P   R   L   L
     SerIleGlyThrSerLeuHisTrpTyrGlnGlnArgThrAsnGlySerProArgLeuLeu
     AGCATTGGCACAAGCTTACACTGGTATCAGCAAAGAACAAATGGTTCTCCAAGGCTTCTC
1081 ---------+---------+---------+---------+---------+---------+ 1140

M   K   Y   A   S   E   S   I   S   G   I   P   S   R   F   S   G   S   G   S
     MetLysTyrAlaSerGluSerIleSerGlyIleProSerArgPheSerGlySerGlySer
     ATGAAGTATGCTTCTGAGTCTATCTCTGGGATCCCTTCCAGGTTTAGTGGCAGTGGATCA
1141 ---------+---------+---------+---------+---------+---------+ 1200
```

-continued

```
              G  T  D  F  T  L  T  I  N  S  V  E  S  E  D  I  A  D  Y  Y
              GlyThrAspPheThrLeuThrIleAsnSerValGluSerGluAspIleAlaAspTyrTyr
              GGGACAGATTTTACTCTTACCATCAATAGTGTGGAGTCTGAAGATATTGCAGATTATTAC
       1201 ---------+---------+---------+---------+---------+---------+ 1260

C  Q  Q  S  H  G  W  P  F  T  F  G  S  G  T  K  L  E  I  K
                 CysGlnGlnSerHisGlyTrpProPheThrPheGlySerGlyThrLysLeuGluIleLys
                 TGTCAACAAAGTCATGGCTGGCCATTCACGTTCGGCTCGGGGACAAAGTTGGAAATAAAA
       1261 ---------+---------+---------+---------+---------+---------+ 1320

CGTAAGTGGACTTTTGTTCATTTACTTGTGACGTTTTGGTTCTGTTTGGGTAGCTTGTGT
       1321 ---------+---------+---------+---------+---------+---------+ 1380

GAATTTGTGATATTT
       1201 ---------+----- 1395.
```

5. A recombinant DNA according to claim 1 comprising an insert coding for a heavy chain murine variable region specific for human CEA which originates from genomic DNA of the cell line CE 25.

6. A recombinant DNA according to claim 1 comprising an insert coding for the polypeptide of formula II wherein $FR_5$, $FR_6$, $FR_7$ and $FR_8$ are polypeptide residues of formula IIA, IIB, IIC and IID, respectively.

7. A recombinant DNA according to claim 1 comprising an insert of the formula

```
                                                                        (IV)
            AAGCTTGTTCTGTTCACATGCAAGGAGGGAAACTAAACTGAGTATGGTGAATCCCTAACC
          1 ---------+---------+---------+---------+---------+---------+ 60

AAAGGGAAAAAATGAAACTACAATATGTTTCAAATGCTGTAACTGAAATCTGGTTTTTTG
         61 ---------+---------+---------+---------+---------+---------+ 120

ATGCCTTATATCTGGTATCATCAGTGACTTCAGATTTAGTCCAACCCCAGAGCATGGTAT
        121 ---------+---------+---------+---------+---------+---------+ 180

AGCAGGAAGACATGCAAATAAGTCTTCTCTCTGCCCATGAAAACACCTCGGCCCTGACCC
        181 ---------+---------+---------+---------+---------+---------+ 240

TGCAGCTCTGACAGAGGAGGCCAGTCCATGGATTTGAGTTCCTCACATTCAGTGATGAGC
        241 ---------+---------+---------+---------+---------+---------+ 300

M  N  F  G  F  S  L  I  F  L  V  L  V
                                  MetAsnPheGlyPheSerLeuIlePheLeuValLeuVal
            ACTGAACACAGACACCTCACCATGAACTTCGGGTTCAGCTTGATTTTCCTTGTCCTTGTT
        301 ---------+---------+---------+---------+---------+---------+ 360

L  K  G
            LeuLysGly
            TTAAAAGGTAATTTATTGAGAAGAGATGACATCTATTTTACGCACATGAGACAGAAAAAA
        361 ---------+---------+---------+---------+---------+---------+ 420

V  Q
                                                                  ValGl
            TGTGGTTTGTTTTGTTAGTGACAGTTTTCCAACCAGTTATTCTCTGTTTGTAGGTGTCCA
        421 ---------+---------+---------+---------+---------+---------+ 480

C  E  V  K  L  V  E  S  G  G  G  L  V  K  P  G  G  S  L  K
               nCysGluValLysLeuValGluSerGlyGlyGlyLeuValLysProGlyGlySerLeuLy
            GTGTGAAGTGAAGCTGGTGGAGTCTGGGGGAGGCTTAGTGAAGCCTGGAGGGTCCCTGAA
        481 ---------+---------+---------+---------+---------+---------+ 540

L  S  C  A  A  S  G  F  T  F  R  T  Y  A  M  A  W  V  R  Q
               sLeuSerCysAlaAlaSerGlyPheThrPheArgThrTyrAlaMetAlaTrpValArgGl
            ACTCTCCTGTGCAGCCTCTGGGTTCACTTTCAGGACCTATGCCATGGCTTGGGTTCGCCA
        541 ---------+---------+---------+---------+---------+---------+ 600

T  P  E  K  R  L  E  W  V  T  S  I  S  S  G  G  T  T  Y  Y
               nThrProGluLysArgLeuGluTrpValThrSerIleSerSerGlyGlyThrThrTyrTy
            GACTCCAGAGAAGAGGCTGGAGTGGGTCACATCCATTAGTAGTGGTGGTACCACCTACTA
        601 ---------+---------+---------+---------+---------+---------+ 660

P  D  S  V  K  G  R  F  T  I  S  R  D  N  A  R  N  I  L  Y
               nProAspSerValLysGlyArgPheThrIleSerArgAspAsnAlaArgAsnIleLeuTy
            TCCAGACAGTGTGAAGGGCCGATTCACCATCTCCAGAGATAATGCCAGGAACATCCTGTA
        661 ---------+---------+---------+---------+---------+---------+ 720
```

-continued

```
         L   Q   V   S   S   L   R   S   E   D   T   A   I   Y   Y   C   A   R   G   F
       rLeuGlnValSerSerLeuArgSerGluAspThrAlaIleTyrTyrCysAlaArgGlyPh
       CCTGCAAGTGAGCAGTCTGAGGTCTGAGGACACGGCCATTTATTACTGTGCAAGAGGTTT
   721 ---------+---------+---------+---------+---------+---------+   780

Y   D   G   Y   L   Y   V   V   D   Y   W   G   Q   G   T   S   L   T   V   S
       eTyrAspGlyTyrLeuTyrValValAspTyrTrpGlyGlnGlyThrSerLeuThrValSe
       CTATGATGGTTACCTCTATGTTGTGGACTACTGGGGTCAAGGAACCTCACTCACCGTCTC
   781 ---------+---------+---------+---------+---------+---------+   840

S
       rSer
       CTCAGGTAAGAATGGCC
   841 ---------+-------   857.
```

8. A recombinant DNA molecule comprising an insert coding for a light chain murine variable region according to claim 1 fused to a human constant region κ or λ.

9. A recombinant DNA according to claim 8 comprising an insert of formula III fused to a human constant region κ.

10. A recombinant DNA molecule comprising an insert coding for a heavy chain murine variable region according to claim 1 fused to a human constant region γ1, γ2, γ3 or γ4.

11. A recombinant DNA according to claim 10 comprising an insert of formula IV fused to a human constant region γ4.

12. A recombinant DNA which is a vector suitable for expression in mammalian hosts comprising:
  (a) an insert according to claim 1
  (b) a complete replicon; and
  (c) one or more dominant marker sequences operably linked to expression control sequences.

13. A recombinant DNA according to claim 1 which is a vector wherein the vector is derived from plasmid pSV.

14. A recombinant DNA which is a vector according to claim 1 wherein the vector is derived from plasmid pSV2gpt or from plasmid pSV2neo.

15. A process for the preparation of the recombinant DNA of claim 1 comprising the steps of
  a) isolating murine DNAs from a suitable hybridoma cell line, selecting the desired DNAs coding for the variable regions of monoclonal antibodies directed against human CEA using DNA probes,
  b) isolating human DNAs from a genomic library, selecting the desired DNAs coding for the constant regions of monoclonal antibodies using DNA probes,
  c) constructing chimeric mouse/human genes by incorporating the DNAs of step a) and b) into appropriate vectors,
  d) transferring the obtained vectors into a recipient host cell, and
  e) selecting and culturing the transformed host cell.

16. A host cell which is transformed with recombinant DNAs according to claim 1.

17. A host cell according to claim 16 which is a mammalian cell of lymphoid origin.

18. A host cell according to claim 16 which is a cell derived from the Ig non-secreting mouse hybridoma cell line Sp2/0 (ATCC CRL 1581).

19. A host cell according to claim 16 which is transformed with one or two vectors according to any of the claims 37–40.

20. A host cell according to claim 16 which is a cell of the cell line EFVIII/γ4Na75-75/CκGa5-6 (CE 75-5-6).

21. A host cell according to claim 16 which is a cell of the cell line EFIX-pCEA-Ig-(γ4;Cκ) (CE 4-8-13).

22. A host cell containing the DNA molecule of claim 1 characterized in that it secretes chimeric monoclonal antibodies consisting of variable regions of mouse origin and human constant regions, which recognizes human carcinoembryonic antigen (CEA), or fragments of said antibodies.

23. A process for the preparation of a host cell according to claim 16 characterized in that a suitable cell is transformed with one or two vectors by electroporation, calcium treatment, microinjection or protoplast fusion.

24. A DNA vector comprising
  (a) an insert selected from the group consisting of an insert coding for a chimeric murine/human light chain according to claim 8, an insert coding for a chimeric murine/human heavy chain according to claim 10, and an insert coding for said murine/human light chain and said murine/human heavy chain;
  (b) a complete replicon; and
  (c) one or more dominant marker sequences operably linked to expression control sequences.

25. A DNA vector comprising
  (a) an insert selected from the group consisting of an insert coding for a chimeric murine/human light chain according to claim 9, an insert coding for a chimeric murine/human heavy chain according to claim 11, and an insert coding for said murine/human light chain and said murine/human heavy chain;
  (b) a complete replicon; and
  (c) one or more dominant marker sequences operably linked to expression control sequences.

* * * * *